United States Patent [19]

Horwitz et al.

[11] Patent Number: 5,824,469
[45] Date of Patent: Oct. 20, 1998

[54] METHOD FOR PRODUCING NOVEL DNA SEQUENCES WITH BIOLOGICAL ACTIVITY

[75] Inventors: Marshall S. Horwitz; Lawrence A. Loeb, both of Bellevue, Wash.

[73] Assignee: University of Washington, Seattle, Wash.

[21] Appl. No.: 316,415

[22] Filed: Sep. 30, 1994

Related U.S. Application Data

[63] Continuation of Ser. No. 105,108, Aug. 11, 1993, abandoned, which is a continuation of Ser. No. 881,607, May 12, 1992, abandoned, which is a continuation of Ser. No. 368,674, Jun. 19, 1989, abandoned, which is a continuation-in-part of Ser. No. 887,070, Jul. 17, 1986, abandoned.

[51] Int. Cl.⁶ ............................. C12Q 1/68; C12N 15/11; C12N 15/10; C12P 19/34
[52] U.S. Cl. ....................... 435/6; 435/91.1; 435/172.3; 435/172.1; 536/23.1; 536/24.1
[58] Field of Search ........................ 435/6, 172.3, 91.1, 435/172.1; 536/23.1, 24.1

[56] References Cited

U.S. PATENT DOCUMENTS

| | | | |
|---|---|---|---|
| 4,725,535 | 2/1988 | Sonenshein et al. | 435/6 |
| 4,888,286 | 12/1989 | Crea | 435/172.3 |

FOREIGN PATENT DOCUMENTS

| | | | |
|---|---|---|---|
| 59-71692 | 4/1984 | Japan . | |
| 2 183 661 | 6/1987 | United Kingdom . | |

OTHER PUBLICATIONS

Research Organics Inc. 1984/85 Catalog, p. 18, 1984.
Childs et al. "Ribosome binding site sequences and function" BIOSIS Accession No. 86:249656, 1986.
Bachman, Barbara J., "Linkage Map of *Escherichia coli* K–12 Edition 7," *Escherichia coli and Salmonella typhimurium*, American Society of Microbiology 2:807–876, 1987.
Vinopal, R.T., "Selectable Phenotypes," *Escherichia coli and Salmonella typhimimurium*, American Society of Microbiology, 2:990–1015, 1987.
Black, Margaret E. and Loeb, Lawrence A., "Identification of Important Residues within the Putative Nucleoside Binding Site of HSV–1 Thymidine Kinase by Random Sequence Selection: Mutants in Vitro," *Biochemistry* 32(43):11618–11626, 1993.
Dube, Dipak et al., "The Association of Thymidine Kinase Activity and Thymidine Transport in *Escherichia coli*," *Gene* 99:25–29, 1990.
Dube, Dipak et al., "Artificial Mutants Generated by the Insertion of Random Oligonucleotides into the Putative Nucleoside Binding Site of the HSV–1 Thymidine Kinase Gene," *Biochemistry* 50(3): 11760–11767, 1991.
Horwitz, Marshall S.Z. and Loeb, Lawrence A. "Promoters selected From Random DNA Sequences," *Proc. Natl. Acad. Sci., USA* 83(19):7405–7409, 1986.

Horwitz, Marshall S.Z. and Loeb, Lawrence A., "DNA Sequences of Random Origin as Probes of *Escherichia coli* Promoter Architecture," *Journal of Biological Chemistry* 263(29):14724–14731, 1988.
Dube, Dipak K. and Loeb, Lawrence A., "Mutants Generated by the Insertion of Random Oligonucleotides into the Active Site of the β–Lactamase Gene," *Biochemistry* 28(14):5703–5707, 1989.
Horwitz, Marshall S.Z. et al., "Selection of New Biological Activities From Random nucleotide Sequences: Evolutionary and Practical Considerations," *Genome* 31(1):112–117, 1988.
Hanahan, Douglas, "Studies on Transformation of *Escherichia coli* with Plasmids," *J. Mol. Biol.* 166(4):557–580, 1983.
Sanger, F. et al., "DNA sequencing with chain–terminating inhibitors," *Proc. Natl. Acad. Sci. USA* 74(12):5463–5467, 1977.
Munir, K.M. et al., Thymidine kinase mutants obtained by random sequence selection, *Proc. Natl. Acad. Sci. USA* 90(9):4012–4016, 1993.
Munir, K.M. et al., "Herpes thymidine kinase mutants with altered catalytic efficiencies obtained by random sequence selection," *Protein Engineering* 7(1):83–89, 1994.
Smith, J. M., Natural selection and the concept of a protein space, *Nature* 225:563–564, 1970.
Hopwood, D.A., *Methods in Microbiology* 3:363–433, 1970.
Davis, B. D., et al., Microbiology, pp. 182–183, Harper & Row, Hagerstown, MD, 1973.
Hall, A., and J. R. Knowles, Directed selected pressure on a β–lactamase to analyze molecular changes involved in development of enzyme function, *Nature* 264:803–804, 1976.
West, Jr. R. W., et al., Construction and characterization of *E. coli* promoter–probe plasmid vectors. I. Cloning of promoter–containing DNA fragments, *Gene* 7271–288, 1979.

(List continued on next page.)

*Primary Examiner*—Jasemine C. Chambers
*Assistant Examiner*—Scott D. Priebe
*Attorney, Agent, or Firm*—Seed and Berry LLP

[57] ABSTRACT

A method of obtaining an oligonucleotide capable of carrying out a predetermined biological function. A heterogeneous pool of oligonucleotides, x+y+z nucleotides in length, is first generated. Each oligonucleotide has a 5' randomized sequence, x nucleotides in length, a central preselected sequence, y nucleotides in length, and a 3' randomized sequence, z nucleotides in length. The resulting heterogeneous pool contains nucleic acid sequences representing a random sampling of the $4^{x+z}$ possible sequences for oligonucleotides of the stated length. A random sampling of the heterogeneous pool of oligonucleotides is introduced into a population of cells that do not exhibit the predetermined biological function. The population of engineered cells is then screened for a subpopulation of cells exhibiting the predetermined biological function. From that subpopulation of cells is isolated an oligonucleotide containing the preselected sequence and capable of carrying out the predetermined biological function.

3 Claims, 7 Drawing Sheets

OTHER PUBLICATIONS

Koshland, D., and D. Botstein, Secretion of beta–lactamase requires the carboxy end of the protein, *Cell* 20;749–760, 1980.

Shortle, D., et al., Segment–direct mutagenesis: construction in vitro of point mutations limited to a small predetermined region of a circular DNA molecule, *Proc. Natl. Acad. Sci. USA* 77(9):5375–5379, 1980.

Old, R. W., and S. B. Primrose, Principles of Gene Manipulation: an introduction to Genetic Engineering, in Studies in Microbiology vol. 2, pp. 93–94, 112–113, and 119–130, University of California Press, Berkeley, CA 1981.

Dalbie–McFarland, G., et al., Oligonucleotide–directed mutagenesis as a general and powerful method for studies of protein function, *Proc. Natl. Acad. Sci. USA* 79:6409–6413, 1982.

Maniatis, T. et al., Molecular Cloning: a Laboratory Manual, pp. 11–17, Cold Spring Harbor Laboratory, 1982.

Shortle, D., et al., Gap misrepair mutagenesis: efficient site–directed induction of transition, transversion, and frameshift mutations in vitro, *Proc. Natl. Acad. Sci. USA* 79:1588–1592, 1982.

Matteucci, M. D., and H. L. Heyneker, Targeted random mutagenesis: the use of ambiguously synthesized oligonucleotdies to mutagenize sequences immediately 5' of an ATG initiation codon, *Nucleic Acids Res.* 11(10):3113–3121, 1983.

Brosius, J., Plasmid vectors for the selection of promoters, *Gene* 27:151–160, 1984.

Geysen, H. M., et al., Use of peptide synthesis to probe viral antigens for epitopes to a resolution of a single amino acid, *Proc. Natl. Acad. Sci. USA* 81:3998–4002, Jul. 1984.

Alberts, B., et al., Antibodies and other macromolecules can be injected into living cells, in Molecular Biology of the Cell, p. 184, Garland Publishing, Inc., New York, NY, 1985.

Barany, F., Two–codon insertion mutgenesis of plasmid genes by using single–stranded hexameric oligonucleotides, *Proc. Natl. Acad. Sic. USA* 82:4202–4206, Jun. 1985.

Bostein, D., and D. Shortle, Strategies and applications of in vitro mutagenesis, *Science* 229(4719):1193–1201, Sep. 1985.

Buell, G., et al. Optimizing the expression in *E. coli* of a synthetic gene encoding somatomedin–C (IGF), *Nucleic Acids Res.* 13(6):1923–1938, 1985.

Craik, C. S. Use of oligonucleotides for site–specific mutagenesis, *BioTechniques*, pp. 12–19, Jan./Feb. 1985.

Geysen, H. M., et al., Small peptides induce antibodies with a sequence and structural requirement for binding antigen comparable to antibodies raised against the native protein, *Proc. Natl. Acad. Sci. USA* 82:178–182, Jan. 1985.

von Heijne, G., Signal sequences: the limits of variation, *J. Mol. Biol.* 184:99–105, 1985.

Hoffman, C. S., and A. Wright, Fusions of secreted proteins to alkaline phosphatase: an approach for studying protein secretion, *Proc. Natl. Acad. Sci. USA* 82:5107–5111, Aug. 1985.

McClure, W. R. Mechanism and control of transcription initiation in prokaryotes, *Ann. Rev. Biochem.* 54;171–204, 1985.

NcNeil, J. B., and M. Smith, Saccharomyces cerevisiae CYCI mRNA 5'–end positioning: analysis by in vitro mutagenesis, using synthetic duplexes with random mismatch base pairs, *Molecular and Cellular Biology* 5(12):3545–3551, Dec. 1985.

Geysen, H. M. et al., The delineation of peptides able to mimic assembled epitopes, in *Synthetic peptides as antigens, Ciba Foundation Symposium* 119, Wiley, Chichester, pp. 130–149, 1986.

Hill, D. E., et al., Saturation mutagenesis of the yeast his3 regulatory site: requirements for transcriptional induction and for binding by GNC4 activator protein, *Science* 234:451–457, Oct. 1986.

Childs, J. D., et al., Corrolating ribosome binding site sequences with function, *J. Cellular Biochem.* Sup. 913, p. 210, Abstract 0960, 1985.

Childs, J. D., et al., Ribosome binding site sequences and function, *UCLA Smp. Mol. Biol.* 30:341–350, 1985.

Kozak, M., Point mutations define a sequence flanking the AUG initiator codon that modulates translation by eukaryotic ribosomes, *Cell* 44:283–292, Jan. 1986.

Hutchinson III, C. A., et al., A complete library of point mutations in the glucocorticoid response element of mouse mammary tumor virus, *Proc. Natl, Acad. Sci. USA* 83:710–714, Feb. 1986.

Schultz, S. C., and J. H. Richards, Site–saturation studies of β–lactamase: production and characterization of mutant β–lactamases with all possible amino acid substitutions at residue 71, *Proc. Natl. Acad. Sci. USA* 83:1588–1592, Mar. 1986.

Porter, S. D., and M. Smith, Homoeo–domain homology in yeast MATα 2 is essential for repressor activity, *Nature* 320:766–768, Apr. 1986.

Tuerk, C., et al., Systematic evolution of ligands by exponential enrichment: RNA ligands to bacteriophage T4 DN4 polymerase, *Science* 249:505–510, 1990.

Lewin, R., The universal constructor set, *New Scientist*, pp. 30–33, 8 Dec. 1990.

*Amersham Research News*, No. 52, pp. 1 and 7–8.

Devlin, J. J. et al., Random peptide libraries: a source of specific protein binding molecules, *Science* 249:404–406, 190.

Scott, J. K., et al., Searching for peptide ligands with an epitope library, *Science* 249:386–390, 1990.

Fig. 6

|  | | | | | | 70 ▶ | | | |
|---|---|---|---|---|---|---|---|---|---|
| Amp (wt) | CGT Arg | TTT Phe | CCA Pro | ATG Met | ATG Met | AGC Ser | ACT Thr | TTC Phe | AAA Lys |
| Non Producer | CGT Arg | *CAT His* | *TTT Phe* | *CTG Leu* | *GGT Gly* | *GTC Val* | *GTT Val* | CAT His | CA |
| Mutant #1 | CGT Arg | TTT Phe | *CCC* Pro | *GTC Val* | ATG Met | AGC Ser | *ATC Ile* | *ATC Ile* | AAA Lys |
| Mutant #2 | CGT Arg | TTT Phe | *CCG* Pro | ATG Met | ATG Met | AGC Ser | *ACA* Thr | *ATA Ile* | AAA Lys |
| Mutant #3 | CGT Arg | TTT Phe | *GCC Ala* | *CTC Leu* | *CTT Leu* | AGC Ser | *ACA* Thr | *TTT* Phe | AAA Lys |
| Mutant #4 | CGT Arg | TTT Phe | *CCT* Pro | *CAA Gln* | *AAT Asn* | AGC Ser | *ACC* Thr | *CAT His* | AAA Lys |
| Mutant #5 | CGT Arg | TTT Phe | CCA Pro | *GTG Val* | *TGT Cys* | AGC Ser | *ACG* Thr | *CAC His* | AAA Lys |
| Mutant #6 | CGT Arg | TTT Phe | *CCC* Pro | *CTT Leu* | *TTG Leu* | AGC Ser | *CAC His* | *CGT Arg* | AAA Lys |
| Mutant #7 | CGT Arg | TTT Phe | *CCC* Pro | *ATA Ile* | *CTA Leu* | AGC Ser | *CCA Pro* | *TCT Ser* | AAA Lys |

# METHOD FOR PRODUCING NOVEL DNA SEQUENCES WITH BIOLOGICAL ACTIVITY

CROSS-REFERENCE TO RELATED APPLICATION

This application is a continuation of U.S. patent application Ser. No. 08/105,108, filed Aug. 11, 1993, now abandoned; which is continuation of U.S. patent application Ser. No. 07/881,607, filed May 12, 1992, now abandoned; which is a continuation of U.S. patent application Ser. No. 07/368,674, filed Jun. 19, 1989, now abandoned; which is a continuation-in-part of U.S. patent application Ser. No. 06/887,070, filed Jul. 17, 1986, now abandoned.

STATEMENT OF GOVERNMENT INTEREST

This invention has been made with government support under grant number OIG R35-CA 39903, awarded by the National Institutes of Health. The government has certain rights in the invention.

FIELD OF THE INVENTION

This invention relates to a method for producing functional, novel DNA sequences using biological selection of random nucleotide sequences, and to the DNA sequences so produced.

BACKGROUND OF THE INVENTION

New methods to rearrange nucleotide sequences in DNA have enriched our understanding of how protein structure governs function. By monitoring the effects of particular substitutions on structure and activity one can explore putative catalytic mechanisms. The most direct approach is to select the region of a gene that codes for the active site of an enzyme and systematically substitute nucleotides based on a knowledge of the amino acid groups, the mechanism for catalysis, and three dimensional structure. This approach has been applied to diverse enzymes including: trypsin (Craik, et al., 1985; see the appended citations), lysozyme (Perry & Wetzel, 1984), and β-lactamase (Dalbadie-McFarland, et al., 1986) with considerable success. We demonstrate here an alternative strategy. Instead of making precise substitution based on detailed knowledge of structure and function, one can insert into genes stretches of nucleotides containing random sequences and use biological selection to obtain new proteins harboring a spectrum of substitutions.

In our initial studies on the selection of nucleotide sequences from random populations, we examined the −35 region of the promoter of the gene for tetracycline resistance (Horwitz & Loeb, 1986; 1988b). We obtained 85 new active promoters, many of which bore little resemblance to the promoter consensus sequence and some of which were more active than the consensus sequence or the wild type tetracycline promoter. We have now remodeled the gene coding for β-lactamase, by replacing DNA at the active site with random nucleotide sequences, and have selected functional active site mutants having altered catalytic activities.

SUMMARY OF THE INVENTION

The invention provides, in one embodiment, a method of obtaining an oligonucleotide capable of carrying out a predetermined biological function. A heterogeneous pool of oligonucleotides, x+y+z nucleotides in length, is first generated. Each oligonucleotide has a 5' randomized sequence, x nucleotides in length, a central preselected sequence, y nucleotides in length, and a 3' randomized sequence, z nucleotides in length. The resulting heterogeneous pool contains nucleic acid sequences representing a random sampling of the $4^{x+z}$ possible sequences for oligonucleotides of the stated length. A random sampling of the heterogeneous pool of oligonucleotides is introduced into a population of cells that do not exhibit the predetermined biological function. The population of engineered cells is then screened for a subpopulation of cells exhibiting the predetermined biological function. From that subpopulation of cells is isolated an oligonucleotide containing the preselected sequence and capable of carrying out the predetermined biological function.

In a related embodiment, the heterogeneous pool of oligonucleotides may be generated from a biased mixture of nucleotides. The heterogeneous pool of oligonucleotides, n nucleotides in length, is synthesized from a mixture of nucleotides consisting essentially of a% adenine, t% thymidine, c% cytosine, and g% guanine, wherein a+t+c+g=100%. The resulting heterogeneous pool contains nucleid acid sequences representing a random sampling of the $4^n$ possible sequences for oligonucleotides of the stated length generated from nucleotides of the stated relative concentrations. A random sampling of the heterogeneous pool of oligonucleotides is introduced into a population of cells that do not exhibit the predetermined biological function. The population of engineered cells is screened for a subpopulation of cells exhibiting the predetermined biological function, and from the subpopulation of cells an oligonucleotide capable of carrying out the predetermined biological function is isolated.

BRIEF DESCRIPTION OF THE DRAWINGS

The details of typical embodiments of the present invention will be described in connection with the accompanying drawings in which:

FIG. 6 shows the active site sequence substitutions obtained as described in Example 8, including the determined nucleotide sequence of each of the carbenicillin resistant mutants, and the deduced amino acid sequences.

DETAILED DESCRIPTION OF THE INVENTION

Figure 1:
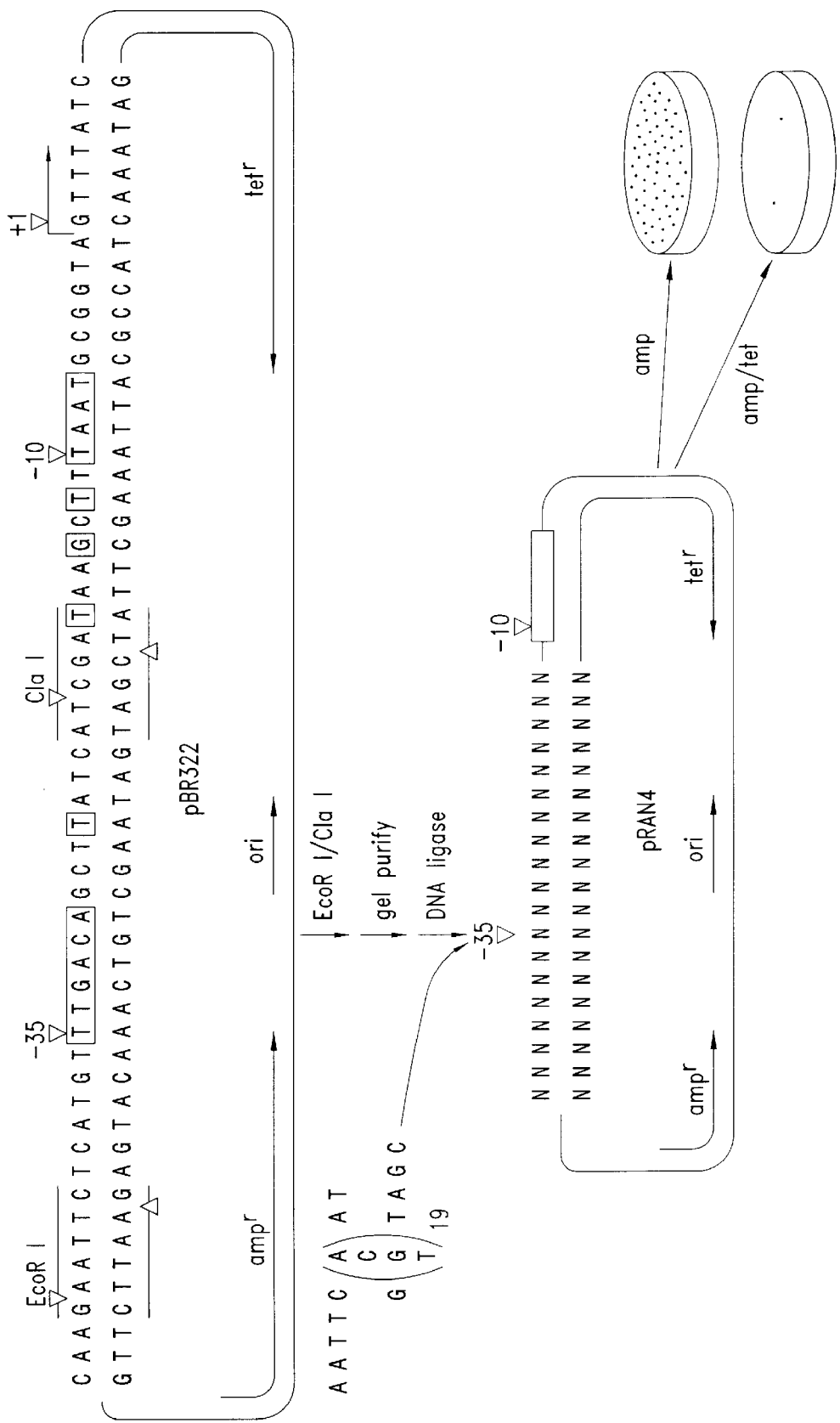
FIG. 1 presents a schematic overview of the representative synthesis, transformation, and selection steps described in Example 1.

The invention provides methods for producing novel, functional DNA sequences using biological selection. To carry out the present invention, a library of all possible DNA sequences is used to transform, transfect or infect suitable, competent host cells. Biological selection is used to isolate functional DNA sequences exhibiting a desired biological activity. The process of the invention is set forth in greater detail in the description and examples that follow.

Synthesis of random DNA sequences. DNA sequences in the form of oligonucleotides can be readily synthesized using various procedures, including phosphoramidite synthesis or phosphotriester chemistry, as described, e.g., in *Oligonucleotide Synthesis: A Practical Approach*, Gait, Ed., IRL Press, Oxford, England (1984), incorporated by reference herein, or may be obtained already synthesized from a commercial source. Synthesis of oligonucleotides has been greatly simplified by automation. Once synthesized, the DNA may be retrieved and purified using techniques, individually or in combination, such as gel electrophoresis, high performance liquid chromatography or thin layer chromatography. A mixed population of oligonucleotides, heterogeneous and random in DNA sequence, may also be produced using these methods. Individual oligonucleotides of lengths up to several hundred basepairs can then be hybridized to one another to construct DNA duplexes for mutagenesis.

In the present invention, the number of possible replacement DNA sequences generated for a given DNA sequence will depend on the number of randomly substituted nucleotide bases in the synthetic oligonucleotides synthesized. For example, for a population of random DNA oligonucleotides, each 19 basepairs in length, there exists a maximum of $4^{19}(3 \times 10^{11})$ different possible replacement sequences (combinations of nucleotide bases).

Cloning of the random DNA sequences. The random DNA sequences synthesized as described above are used to transform prokaryotic or eukaryotic cells. The DNA may be introduced using cloning vectors including plasmids, vectors capable of integrating into host cell chromosomes, for example, bacteriophage lambda, other bacteriophages (e.g., the M13 family of filamentous bacteriophage vectors described by Messing (in *Methods in Enzymology*, 101, pp. 20–78, Academic Press (1983)), viruses, or cosmids, or by vectorless gene transfer wherein linearized DNA containing the gene of interest is added directly to a culture of host cells, resulting in transformation of the cells. Glover, D. M., in *Gene Cloning: The Mechanics of DNA Manipulation*, London, Chapman and Hall (1984). Other methods of introducing DNA into a cell may also be used, for example, direct injection such as microinjection, or using sperm carriers.

Insertion of random DNA sequences. Where a vector is used as the cloning vehicle, the vector chosen may be altered by deleting a particular region of DNA known to contain a functional site, for example, the promoter recognition site for a particular gene, using standard methods, such as cleavage by restriction enzymes, to insert the synthetic random DNA sequences. The termini of random DNA sequences, synthesized as described above, may be modified so as to be easily inserted into the vector selected. For example, sequences with "sticky" ends generated by cleavage by restriction enzymes may be inserted into a vector which has been digested using the same enzymes. The random DNA sequences are then inserted into the vector with a ligation enzyme, for example, the enzyme T4 DNA ligase, using standard techniques such as those described by Maniatis, et al., in *Molecular Cloning: A Laboratory Manual*, Cold Spring Harbor, N.Y. (1982), incorporated by reference herein.

The random DNA sequences may also be directly inserted into a vector without removing any DNA, for example, to select for DNA sequences encoding a novel protein. Random sequences may thus be introduced into an open reading frame (a DNA sequence encoding a protein and containing appropriate regulatory elements for translation including a promoter, ribosome binding site, translation initiation codon, and stop codon) by ligating the random fragments to the appropriate genetic regulatory elements, such as transcription and translation initiators, for example the promoter, or Shine-Dalgarno ribosome binding site.

Expression of recombinant DNA. The recombinant DNA vectors containing the inserted randomly synthesized DNA sequences are then used to transform or transfect suitable host cells such as bacteria. An example of a suitable bacterium is *E. coli*. If *E. coli* bacteria are used as a host, a preferred method for transformation is the high efficiency technique described by Hanahan, *J. Mol. Biol.*, 166, pp. 557–580 (1983), incorporated by reference herein. Host cells are then grown in an antibiotic, such as ampicillin, to select for those cells which contain recombinant plasmids carrying the cointroduced random DNA sequences.

The recombinant DNA may then be purified from host cell preparations and sequenced using well-known procedures to verify that it contains the inserted synthetic DNA sequences, and to reveal the sequence of the inserts.

Biological selection. The methods of the present invention use biological selection of randomly synthesized DNA sequences to identify and isolate those sequences that exhibit a desired biological function. To accomplish such selection, a procedure for detecting the desired functional activity must be chosen. In Examples 1–5 below, the function selected for is the ability to promote transcription of the gene for tetracycline resistance. In these examples, the antibiotic tetracycline is used to select for those synthetic DNA sequences able to function as promoters for transcription of the tetracycline resistance gene, as determined by the ability of *E. coli* cells carrying plasmids to grow in the presence of the antibiotic.

Novel DNA sequences capable of a different function, for example "leader" sequences (also known as "signal sequences"), may also be selected from a population of random DNA fragments. Leader sequences allow for the transmembrane insertion or extracellular secretion of cellular proteins, and are common to both prokaryotes and eukaryotes. Leader sequences from different proteins are composed predominately of hydrophobic amino acid residues and range in length from 13 to 36 amino acid residues. Alberts, B. M., et al., in *Molecular Biology of the Cell*, New York, Garland Publishing, Inc., (1983). While a consensus leader sequence has been established for several proteins (Kretsinger, R. H. & Creutz, C. E., *Nature*, 320 p. 573 (1986)), the leader sequences of most proteins differ considerably and contain no homology to each other, (von Heijne, G., *J. Mol. Biol.*, 184 pp. 99–105 (1985)), suggesting that a great variety of protein sequences may possess this secretory function. Leader sequences may be identified, e.g., by using a gene for a secreted protein, such as β-lactamase, capable of conferring positive growth selection. β-lactamase is secreted extracellularly and protects cells from attack by antibiotics, such as ampicillin (Alberts et al., supra). The 5' portion of the β-lactamase gene of the plasmid pBR322 contains 66 nucleotides coding for a 23 amino acid residue leader sequence of the protein product. Ambler, R. P. & Scott, G. K., *Proc. Nat'l. Acad. Sci. (USA)*, 75, pp. 3732–3736 (1978); and Sutcliffe, J. G. *Proc. Nat'l Acad. Sci. (USA)*, 75, pp. 3737–3741 (1978). Frameshift mutations, point substitutions, and deletion mutations in this region of the gene produce defective proteins that are not secreted from the cell. Koshland, D. *A Genetic Analysis of Beta-lactamase*, Ph.D. thesis, Mass. Inst. Technol., Cambridge (1982). Consequently, bacteria harboring plasmids with nonfunctional mutations in the leader sequence of the β-lactamase gene are sensitive to the antibiotic ampicillin, whereas bacteria harboring plasmids with intact β-lactamase genes are resistant to ampicillin. As a result, host cells containing vectors with inserted DNA sequences not capable of functioning as β-lactamase leader sequences will not survive in media containing the antibiotic ampicillin. However, cells which do secrete β-lactamase and survive in media containing the antibiotic will contain vectors having synthetic DNA sequences capable of functioning as leader sequences, and these sequences may then be readily isolated and sequenced as described above.

In addition, growth selection using the present invention may be used to select DNA sequences capable of encoding novel proteins. Random DNA sequences may contain unique sequences that are capable of coding for biologically active proteins. Thus, long, random DNA fragments may be ligated into a vector such as a plasmid vector containing the regulatory elements for gene expression, including DNA encoding promoter and ribosome binding sites. The resulting vector will thus be able to transcribe random proteins from the randomly generated open reading frame. A heterogeneous population of plasmids, each coding for a unique, random protein may be used to transform appropriate eukaryotic or prokaryotic host cells such as *E. coli* cells. From these cells, proteins possessing novel catalytic activity may be identified using growth selection. Alternately, to isolate a novel protein capable of degrading a particular plastic, the transformants may be grown on media, for example, Luria-Bertani (LB) agar, covered with the particular plastic as a growth barrier, and then layered with more media (e.g., LB agar). Bacterial clones containing random DNA sequences conveying plastic-degrading activity will penetrate the plastic barrier to grow in the topmost layer of agar. An example of the use of this invention to select DNA sequences encoding novel proteins from a population of random DNA sequences is described below, in Example 7.

From the foregoing, it can be appreciated that the biological selection of the present invention provides a technique for screening large numbers of random, synthetic DNA sequences to identify those novel sequences capable of carrying out the chosen function. The present invention does not require characterization (e.g., sequencing, hybridization, and other procedures) of the synthesized DNA sequences prior to the selection process, thereby eliminating the need for tedious and time-consuming manipulations.

Other parameters useful for biological selection based on the ability of transformed cells to grow in certain media, in addition to antibiotic resistance, include resistance to toxins such as metals and environmental pollutants such as polychlorinated biphenyl (PCB), and the ability to grow in media containing or lacking specific metabolites, for example, in the presence of unusual carbon sources including oils and environmental pollutants.

The present invention may also be used to select for novel, synthetic DNA sequences capable of encoding a peptide which exhibits the biological activity of the peptide encoded by the natural (wild-type) DNA sequences, or for entirely new, functional peptides. Standard assays may be used to detect the presence or absence of expressed peptide in a growth medium or even within the host cells. For example, visually screenable assays to indicate the presence of a peptide using enzyme and enzyme substrate reactions to generate a color signal, such as the blue color produced by β-galactosidase in the presence of sugar analogs, may be used. The expressed peptide must then be tested for the ability to carry out the function of the corresponding wild-type DNA peptide or to determine whether a peptide exhibiting the new function has been produced.

Examples 1 through 5 below, describe representative protocols for obtaining novel, synthetic DNA sequences with promoter activity. A comparison of known RNA polymerase-binding sites of different genes of *E. coli* reveals two highly conserved promoter elements centered at about 10 and 35 nucleotide basepairs upstream from the start of transcription. Pribnow, *J. Mol. Biol.*, 99, pp. 419–443 (1975); Schaller et al., *P.N.A.S. USA*, 72, pp. 737–741 (1975); Takanami, et al., *Nature*, 260, pp. 297–302 (1976); Seeburg, et al., *Eur. J. Biochem.*, 74, pp. 107–113 (1977); and Rosenberg and Court, *Ann. Rev. Genet*, 13, pp. 319–353 (1979). The involvement of each nucleotide in the initiation of transcription has been inferred largely from an analysis of mutations. Rare mutations that increase transcription (so-called "up" mutations) usually increase homology with the consensus sequence and spacing, while the more common mutations that decrease transcription ("down" mutations) usually decrease homology with the consensus sequence and spacing. McClure, supra. Nevertheless, as demonstrated by the present invention, sequences that greatly differ from the consensus sequence can still function as promoters.

The present invention uses random mutagenesis to produce novel, synthetic DNA sequences which are capable of exhibiting biological activity, although such sequences may substantially deviate from known, wild-type sequences having that same function in nature. The process described above and in the Examples which follow, extends beyond the use of mutagenesis merely as a tool to study the nature of regions of DNA encoding specific biological activity. The present invention uses significantly expanded random mutagenesis, i.e., heterogeneity, at a substantial number of nucleotide bases within a DNA sequence, to produce novel, functional sequences. Furthermore, the use of selection pressure, e.g., binding a preselected antigen, provides an efficient, cost-effective and rapid means for screening large numbers of synthetic DNA sequences to isolate those novel DNA sequences capable of, e.g., coding for an immunological variable region of desired specificity.

In summary, the invention provides a method of obtaining an oligonucleotide capable of carrying out a predetermined biological function. First, a heterogeneous pool of oligonucleotides is generated. The oligonucleotides are typically n nucleotides in length, and the nucleic acid sequences of the oligonucleotides in the heterogeneous pool typically represent a random sampling of the $4^n$ possible sequences for oligonucleotides of that length. A random sampling of the heterogeneous pool of oligonucleotides is introduced into a population of cells that do not exhibit the predetermined biological activity. The population of cells is thereafter screened for a subpopulation of engineered cells that does exhibit the predetermined biological function. From the subpopulation of cells, an oligonucleotide capable of carrying out the predetermined biological function is isolated.

In the practice of the invention, the randomized oligonucleotide can range in length (n) from about 3 or more (or 1 codon or more, if the oligonucleotide is to be expressed) to several hundred or more nucleotides in length. It is generally preferable to limit the size of the randomized oligonucleotide to about 24 bases, coding for 8 amino acids, as this will potentially produce a heterogeneous pool of about $8^{20}$ or a billion different oligonucleotides, which is convenient for screening.

The randomized oligonucleotide may alternatively include first and second randomized regions (x and z nucleotides in length, respectively) that flank on either side a linker region (y nucleotides in length) of preselected sequence. The heterogeneous pool of these tripartite oligonucleotides represents a random sampling of the $4^{x+z}$ possible sequences of such oligonucleotides of that length (x+y+z). A random sampling of this heterogeneous pool of oligonucleotides is in turn introduced into a population of cells that do not exhibit the predetermined biological function. The population of cells is thereafter screened for a subpopulation of cells exhibiting the predetermined biological function. That is, the functionality of the tripartite oligonucleotides is screened as a unit. From the selected subpopulation of cells, an oligonucleotide containing the linker sequence and capable of carrying out the predetermined biological function is isolated. Representative protocols are set forth in Example 8 below. The linker sequence can correspond with a native sequence or can be a novel sequence that is present by design in all of the randomized oligonucleotides. For example, a codon for serine in a native sequence can be changed in a preselected manner to a codon for another nucleophilic amino acid, such as cysteine.

In this embodiment, the overall length of the randomized portion of the oligonucleotide (x+z) is preferably held to no more than about 24 bases. The individual and relative lengths of the flanking randomized and central conserved sequences are not critical and may be dictated by site-specific considerations, such as a previously observed association of the linker sequence with the screened function.

As described above, the nucleotide composition of the randomized oligonucleotide region(s) may alternatively be biased in favor of or away from any of adenine, thymidine, cytosine, and/or guanine. Such biasing is conveniently accomplished by adjusting the relative concentrations of the dNTPs from which the oligonucleotides are randomly synthesized. In other words, the relative concentrations of A, T, C, and G need not be about 25% each, e.g., A may constitute a%; T, t%; C, c%; and G, g%; provided that a+t+c+g=100%. The resulting heterogeneous pool of oligonucleotides, n nucleotides in length, will nevertheless have nucleic acid sequences representing a random sampling of the $4^n$ possible sequences for oligonucleotides of that length synthesized from a pool of nucleotides having such preadjusted relative concentrations.

The following Examples are presented to illustrate the present invention and to assist one of ordinary skill in making and using the same. The examples are not intended in any way to otherwise limit the scope of the disclosure or the protection granted by the Letters Patent hereon.

EXAMPLE 1

Production of Novel DNA Sequences With Promoter Activity

In this Example, novel DNA sequences capable of functioning as promoters in the tetracycline resistance gene were produced by: (1) chemical synthesis of a heterogeneous population of DNA fragments, 19 basepairs in length, with the nucleotide at each position of the 19 basepairs being random; (2) insertion of these DNA fragments into pBR322 plasmids with segments of DNA deleted in the region of the plasmid known to encode for promoter recognition; (3) transformation of *E. coli* bacteria with the recombinant plasmid; and, (4) selection of transformed host cells by growth in media containing the antibiotic tetracycline. These steps are summarized in FIG. 1 and described in detail below.

Restriction enzymes used in this Example were purchased from Bethesda Research Laboratories (Gaithersburg, Md.), Boehringer Mannheim (Indianapolis, Ind.), and New England Biolabs (Beverly, Mass.), and, except where indicated, use of these enzymes followed the manufacturers' directions. The enzymes T4 DNA ligase, T4 polynucleotide kinase, large fragment of DNA polymerase I (Klenow Fragment), and bacterial alkaline phosphatase were purchased from Bethesda Research Laboratories. Nick-translation reagents (including DNA polymerase I and DNase 1) were purchased from New England Nuclear (Boston, Mass.) and used according to the manufacturer's instructions.

Verification of the promoter recognition sequence in pBR322. Prior to synthesis of the random population of DNA sequences, the region of plasmid DNA containing the promoter recognition sequence for transcription of the tetracycline resistance gene was deleted using restriction enzymes to verify the importance of this region for the transcription of that gene.

The plasmid pBR322 contains a DNA sequence corresponding to the tetracycline resistance gene, encoding a single, noninducible 43.5 kilodalton polypeptide (Blackman and Boyer, *Gene,* 26, pp. 197–203 (1983)) that functions at the cell membrane to block accumulation of the antibiotic tetracycline. McMurry et al., *P.N.A.S. USA,* 77, pp. 2974–3977 (1980). The transcription initiation site for the gene has been identified by S1-nuclease protection. Brosius et al., *J. Biol. Chem.,* 257, pp. 9205–9210 (1982). In addition, the position of the promoter recognition site for the tetracycline resistance gene has been deduced from: (1) promoter consensus sequence homology in pBR322 (Sutcliffe, *Cold Spring Harbor Symp. Quant. Biol.,* 43, pp. 77–90 (1979)); (2) deletion mutations (Rodriquez et al., *Nucl. Acids. Res.,* 6, pp. 3267–3287 (1979)); and (3) electron microscopic mapping (Stuber and Bujard, *P.N.A.S. USA,* 78, pp. 167–171 (1981)).

FIG. 1 shows the tetracycline resistance gene promoter sequence as described by Sutcliffe, supra. Portions of this promoter sequence that correspond to the −10 position and −35 promoter recognition site of the consensus sequence are shown in boxes. Hawley and McClure, *Nucl. Acids Res.,* 11, pp. 2237–2255 (1983). In FIG. 1 the letter "N" indicates unspecified bases. Restriction enzyme cleavage sites for the endonucleases EcoRI and Cla I flank the promoter recognition site in the tetracycline resistance gene. A plasmid designated as pBdEC with a 22 basepair deletion in the promoter recognition site, extending from the −43 position (in the EcoRI site) to −21 (in the Cla I site) was constructed by digesting pBR322 DNA with EcoRI and Cla I, purifying the larger DNA fragment by electrophoresis in low melting temperature agarose (Bethesda Research Laboratories), filling in the 5' overhangs with the large fragment of DNA polymerase I in the presence of all four deoxynucleoside triphosphates, and recircularizing the blunt-ended fragment with T4 DNA ligase, using the procedures detailed in Maniatis, supra. The expected deletion was confirmed by DNA sequence analysis.

Figure 3:
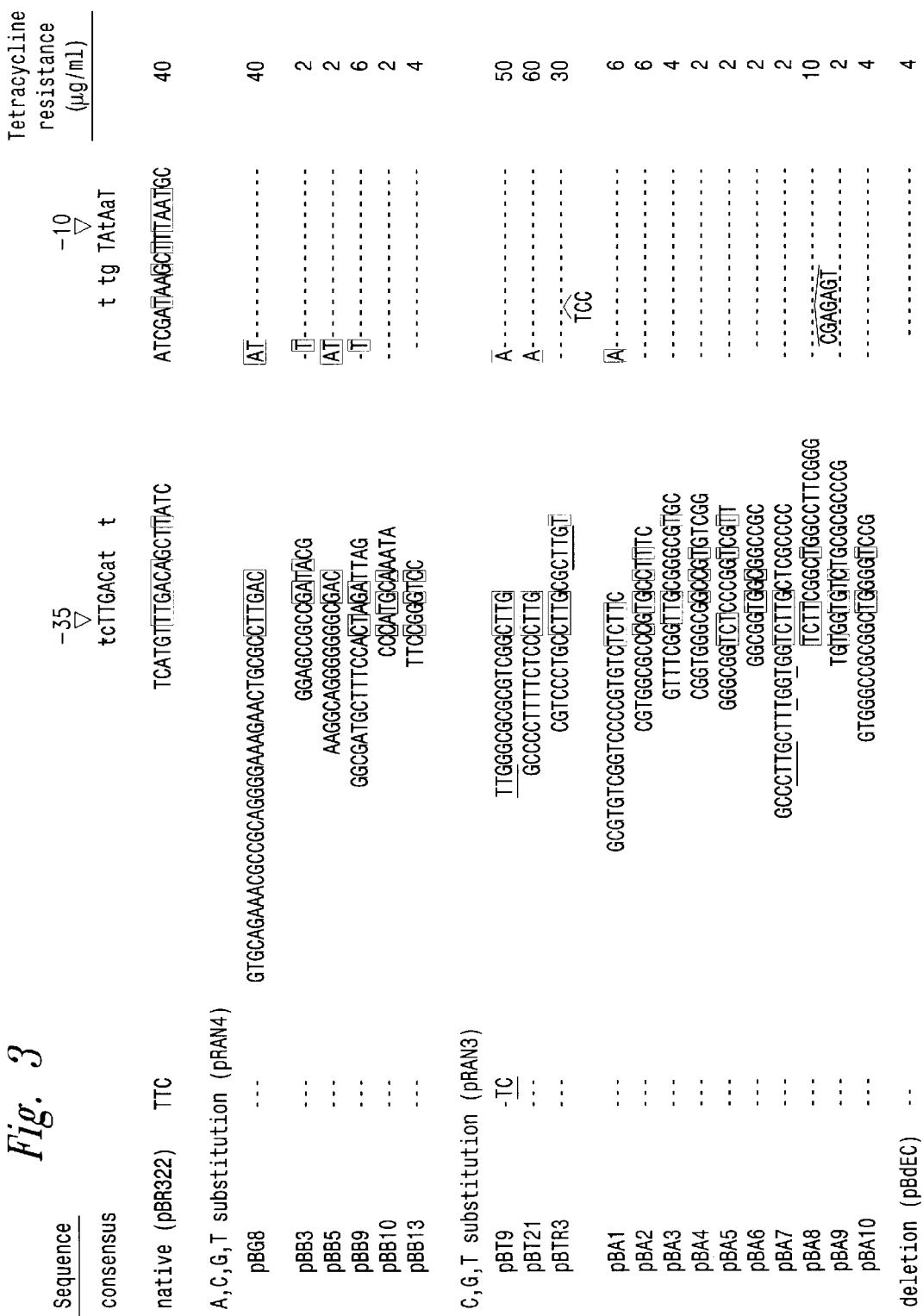
FIG. 3 shows the substitutions made in the wild type promoter sequence for the tetracycline resistance gene, as described in Examples 1 through 5 and summarized in the Discussion following Example 5.

The recircularized plasmids were used to transform *E. coli* strain AG1 (Stratagene Cloning Systems, San Diego, Calif.), and *E. coli* found to contain the recombinant plasmid were cultured in the presence of both tetracycline and ampicillin. The manufacturer's protocol for transformation using these plasmids was followed. Briefly, transformed host cells were grown in LB for one hour (approximately two generations) prior to antibiotic selection on LB-containing agar. Ampicillin concentration in the agar was 50 μg/ml. The transformation efficiency was approximately 5×10³ colonies/pg of ligated DNA. The bacteria were found to be resistant to a tetracycline concentration of 2 μg/ml in the absence of a plasmid, to a concentration of 40 μg/ml when harboring the plasmid pBR322, and to only 4 μg/ml when harboring pBdEC (the plasmid with the promoter recognition site deleted, as described above). The DNA sequence in which the promoter recognition site has been deleted is depicted in FIG. 3.

Transcription of the tetracycline resistance gene was identified by northern blot analysis using the procedure as described by Maniatis et al., supra. Briefly, in this procedure, 5 μg of nucleic acids (DNA and RNA) were purified from the *E. coli* AG1 harboring the pBdEC plasmid, using standard procedures, such as described by Brosius et al., *J. Biol. Chem.*, 257, pp. 9205–9210 (1982), incorporated by reference herein. 114 ng of the extracted pBR322 DNA was electrophoresed on 1% agarose gel containing 2.2M formaldehyde. The gel was then transferred to hybridization membranes (New England Nuclear) and screened using the 787 basepair, $^{32}$P-labeled, nick-translated EcoRV to Nru I restriction fragment probe from the coding region of the tetracycline resistance gene in pBR322. Filter hybridization was performed according to the manufacturer's instructions (New England Nuclear) and was conducted at 42° C. in 10% dextran sulfate, 1M NaCl, and 1% NaDodSO$_4$. Filters were washed in 2×SSC and 1% NaDodSO$_4$ and then 0.1×SSC at 25° C. (1×SSC is 0.15M NaCl/15 mM sodium citrate, pH 7.0). Maniatis et al., supra. The Hind III digest of bacteriophage lambda λ DNA was used as a size marker. Ethidium bromide staining of the agarose gel in the absence of formaldehyde was used to ensure that all lanes contained equal amounts of DNA. The autoradiogram (FIG. 2) was exposed for 8 hours at room temperature on XAR film (Eastman Kodak, Rochester, N.Y.). A GS 300 Scanning Densitometer (Hoefer Scientific Instruments, San Francisco, Calif.), which measures the degree of exposure of the film proportional to the intensity of the radiation in the autoradiogram, was used to quantify hybridization. As can be seen from FIG. 2, deletion of the promoter recognition sequence results in absence of transcription of the tetracycline resistance gene.

Synthesis of oligonucleotides. A heterogeneous population of DNA segments which were random in sequence at each of the 19 basepairs thereof was synthesized by the phosphoramidite method, using an Applied Biosystems 380A DNA synthesizer (Foster City, Calif.), and purified by thin layer chromatography as described by Alvarado-Urbina, et al., in *Science*, 214, pp. 270–274 (1981), incorporated by reference herein. The oligonucleotides were synthesized using approximately equimolar mixtures of phosphoramidites at each coupling step. The population of recombinant plasmids produced by insertion of these synthetic DNA sequences therein, as described below, could yield up to a maximum of $4^{19}$ (or approximately $3\times10^{11}$) different replacement sequences.

An 8-basepair (bp)-long oligomer, 5'-GGATCGAT-3', was hybridized to an oligomer 35 bp long, 5'-CCGAATTC(A, C,G,T)$_{19}$ATCGATCC-3', in a 2:1 molar ratio, extended with the large fragment of DNA polymerase I, and digested with an excess of the enzymes EcoRI and Taq 1. The 8-bp oligomer (10.8 μg) and the 35-bp oligomer (24 μg) were annealed in 90 mM NaCl, 15 mM tris-HCl (pH 7.9), and 1 mM MgCl$_2$ in a total volume of 120 μl by heating at 65° C. for 5 min and then at 57° C. for 90 min, followed by immediate chilling on ice for 15 min. Water and other reagents were added to this reaction to bring the final volume to 240 μl containing 45 mM NaCl, 3 mM MgCl$_2$, 1 mM dithiothreitol, 100 μM of each of the four dNTPs and 16 units of the large (Klenow) fragment of DNA polymerase I. The reaction was incubated for 1 hour at 25° C. and then terminated by purification on NENSORB columns (New England Nuclear). The eluate was dried under a vacuum, resuspended in 150 μl containing 50 mM Tris-HCl (pH 8.0), 10 mM MgCl$_2$, 50 mM NaCl, and 250 units of the enzyme Taq I. The reaction mixture was incubated for 21 hours at 37° C. 5 μl containing 50 units of Taq I were added, and incubation continued for an additional 8 hours at 37° C. 55 μl (250 units) of EcoRI was then added, and incubation continued for an additional 16 hours at 37° C. Progress of the digestion was monitored by electrophoresis of the dephosphorylated and $^{32}$P-kinased DNA fragments on a 12% polyacrylamide with 7M urea sequencing gel, as described by Perbal, in *A Practical Guide to Cloning*, Wiley-Interscience Pub., New York (1984). The restriction fragments were purified by phenol extraction followed by ethanol precipitation. Approximately 8 μg of double-stranded DNA derived from the synthesized oligonucleotides was thereby obtained, a portion of which was inserted into the plasmid pBR322 as described below.

Plasmid construction. Plasmids containing the heterogeneous population of synthesized and duplexed oligonucleotides, collectively denoted as plasmid "pRAN4," were produced by digesting pBR322 with the enzymes EcoRI and Cla I, removing 5' phosphates with bacterial alkaline phosphatase, purifying the resulting large DNA fragment by electrophoresis in low melting temperature agarose gel, and ligating the appropriate double-stranded DNA restriction fragment obtained as described above with the vector DNA in a 20:1 DNA insert to vector molar ratio using T4 DNA ligase. Maniatis et al., supra. The sequences of the random DNA fragments contained in the plasmids within the pRAN4 population are indicated in FIG. 3 (plasmids pBG8, pBB3, pBB5, pBB9, pBB10, and pBB13).

Transformation. Competent *E. coli* cells, strain AG1 (recA1) prepared as described by Hanahan, *J. Mol. Biol*, 166, pp. 557–580 (1983), incorporated by reference herein, were purchased from Stratagene Cloning Systems and used for high efficiency transformation. All transformed colonies were grown in Luria-Bertani agar containing 0.1% w/v glucose for 60 minutes (approximately two generations) prior to antibiotic selection. The transformants were then placed in LB agar containing 50 μg/ml ampicillin to identify bacteria carrying recombinant plasmids with functional random DNA inserts.

*E. coli* AG1 was transformed using 410 ng of DNA from the pRAN4 plasmid population, obtained as described above, at an efficiency of $10^3$ to $10^4$ colonies/μg DNA using ampicillin selection and 10 to $10^2$ colonies/μg DNA with ampicillin and tetracycline selection. Table 1 shows the number of colonies produced by transformation using pRAN4 (1A) and two other plasmid populations, pRAN3 and pBT9R (described below).

TABLE 1

Transformation With Random Plasmid Populations

| | | amp selection | | | amp and tet selection | | | |
| --- | --- | --- | --- | --- | --- | --- | --- | --- |
| | | Colonies, | Sequences, no. | | Colonies, | Sequences, no. | | |
| | DNA | No. | pBR322 | Deletions | Inserts | No. | pBR322 | Deletions | Inserts |
| A. | pRAN4 | 125 | 2 | 3 | 5 | 28 | 27 | 0 | 1 |
| B. | pRAN3 | 887 | 0 | 0 | 10 | 23 | 21 | 0 | 2 |
| C. | pBT9R | 353 | | | | 114 | 0 | 0 | 4 |

Ampicillin selection yielded 125 colonies. To determine the nature of the DNA insertions present, plasmids from 10 of these ampicillin resistant colonies were characterized by size fractionation using electrophoresis on 1% agarose slab gels and DNA sequence analysis (dideoxy chain termination method). Two plasmids were found to be identical to plasmid pBR322, and three plasmids containing deletions bounded by the EcoRl and Cla I sites were identified (sequences not shown). These plasmids are assumed to be part of a background of about 50% of the vectors which either escaped digestion with restriction enzymes or ligation of the inserted DNA sequence. The remaining five plasmids, pBB3, pBB5, pBB9, pBB10, and pBB13, were found to contain promoter substitutions of from 10 to 23 basepairs in length (FIG. 3). Of a total of 77 bases substituted among these five plasmids, the average insert length was 15 basepairs long and the composition was 22% adenine, 27% cytosine, 34% guanine and 17% thymine.

Biological selection using tetracycline. Tetracycline resistance was used for biological selection for promoter activity in plasmids containing promoter substitutions of synthetic DNA sequences. The tetracycline resistance gene of pBR322 previously has been used as a promoter probe. Widera, et al., *Molec. Gen. Genet.*, 163, pp. 301–305 (1978); Neve et al., *Nature*, 277, pp. 324–325 (1979); and West and Rodriquez, *Gene*, 7, pp. 291–304 (1982). In these experiments, the promoter typically was inactivated by deletion within the recognition site. Restriction digests of genomic DNA from prokaryotes and eukaryotes were ligated into the inactive promoter region as a test of their potential to restore promoter function. Depending upon the organismal source of the DNA, insertions with promoter activity were selected at a frequency of 0.2 to 33% from among all recombinants. In the absence of DNA sequence data, this high frequency of promoter selection was explained as either verification of functional promoters (West et al., *Gene*, 7, pp. 271–288 (1979)) or as fortuitous restoration of the deleted portion of the native promoter. Brosius, *Gene*, 27, pp. 151–160, (1984).

Tetracycline resistance of the *E. coli* containing plasmids with inserted synthetic DNA sequences was determined by the efficiency of plating-50% method ($EOP_{50}$) described by West et al. in *Gene*, 7, pp. 271–288 (1979). Test colonies were inoculated using a sterile needle on LB agar with 0.1% (w/v) glucose, containing 0, 1, 2, 4, 6, 8, 10, 16, 20, 30, 40, 50, 60, 70, 80, 90, and 100 µg/ml tetracycline. Inhibitory values were defined as those which reduced growth, as measured by reduction to one-half the number of viable colonies.

Ampicillin and tetracycline selection in combination yielded 28 colonies. To characterize the plasmids from all 28 colonies to determine if any contained promoter sequences, plasmids were purified for gel electrophoresis sizing and DNA sequencing by lysing the host *E. coli* cells by brief treatment with lysozyme (Sigma Chemical Co., St. Louis, Mo.), then detergent and sodium hydroxide. Cell debris was pelleted by centrifugation, and the plasmid was purified from the cleared supernatant using ethanol precipitation. Maniatis, et al., supra. Plasmid sizes were then compared using agarose gel electrophoresis, and about 200 nucleotide basepairs centered at the promoter recognition site were sequenced. DNA sequencing was conducted using the dideoxy chain termination method (Sanger et al., *P.N.A.S.* (*USA*), 74, pp. 5463–5467 (1977), incorporated by reference herein, directly from double-stranded pBR322 templates from these rapid preparations. (Wallace et al., *Gene*, 16, pp. 21–26 (1981)). 27 plasmids were found to be identical to pBR322. Again, these are from the background of unmodified vectors because it is improbable that a promoter sequence identical to pBR322 would be present within the small subpopulation of all random sequences selected here. The other plasmid, pBG8, contained a 38 basepair promoter substitution (FIG. 3). Although there was sequence length heterogeneity, the average length of all the pRAN4 substitutions including those not selected for tetracycline was 19 bases, in agreement with the length of the synthetic DNA sequences. Therefore, approximately half of the 125 ampicillin resistant colonies contained plasmids with promoter substitutions and about 1 out of 63 colonies was also tetracycline resistant. These results suggest that approximately 2% of the $3\times10^{11}$ possible random sequences may duplicate promoter recognition site activity.

EXAMPLE 2

Production of Novel DNA Sequences Lacking Adenine with Promoter Activity

To verify that the synthetic restriction DNA fragments were responsible for the observed sequence heterogeneity at the promoter recognition site, and to check for allowable sequence diversity, a population of plasmids, "pRAN3," was prepared so as to be deficient in the nucleotide base adenine in the sense strand throughout the randomly substituted sequences of DNA. Thus, oligonucleotides were synthesized using an 8-bp oligomer, 5'-GGATCGAT-3', annealed to a 35-bp oligomer, 5'-CCGAATTC(C,G,T)$_{19}$ATCGATCC-3' oligomer, using the procedures described in Example 1 for synthesis of oligonucleotides. The random plasmid population pRAN3 was produced as described above for pRAN4 in Example I, by digesting pBR322 with Eco RI and Cla I, removing 5' phosphates with bacterial alkaline phosphatase, purifying the larger fragment by electrophoresis, and ligating these randomly synthesized DNA fragments deficient in adenine using T4 DNA ligase. Plasmid population pRAN3 contains the sense-strand promoter recognition site substitutions of random 19 base sequences of cytosine, guanine, and thymine. For this population, there is a maximum of $3^{19}$ (or approximately $10^9$) different, possible replacement sequences. *E. coli* bacteria strain AG1 was transformed using 410 ng of pRAN3, as described in Example 1 for transformation using pRAN4 DNA, at an efficiency of $10^3$ to $10^4$ colonies/µg DNA using ampicillin selection and 10 to $10^2$ colonies/µg DNA with ampicillin and tetracycline selection.

The results of transformation using pRAN3 plasmids are shown above in Table 1B. Equal amounts of DNA were used for each antibiotic selection. Ampicillin selection yielded 887 colonies. Plasmids from 10 of these ampicillin resistant colonies were characterized. All 10 of these plasmids, pBA1 through pBA10, contain replacement insertions of from 15 to 29 nucleotide basepairs (FIG. 3), implying that greater than 90% of the plasmids in pRAN3 contain promoter substitutions. Of the total of 203 bases substituted among these 10 plasmids the average insert length was 20, and the composition was 0% adenine, 32% cytosine, 42% guanine, and 26% thymine. Because the sequence of the inserted DNA determines the final sequence composition of the plasmid, these results indicate that the sequence heterogeneity results from ligation of the random DNA insert and not from a cellular process randomly mutating nucleotides within a sequence.

Ampicillin and tetracycline selection yielded 23 colonies. Plasmids from all 23 of these ampicillin/tetracycline resistant colonies were characterized using plasmid purification and sequencing procedures as described in Example 1. 21 plasmids were identical to pBR322. The inclusion of adenine in these promoter sequences indicates that these are from the background of unmodified vectors and are not present within the small subpopulation of all random sequences selected here. The other two plasmids, pBT9 and pBT21, contain promoter substitutions of 19 and 17 nucleotide basepairs, respectively, lacking adenine (FIG. 3). An additional tetracycline resistant colony containing a plasmid, pBTR3 (FIG. 3), was detected using replica plating of the colony growing on the ampicillin media onto ampicillin/tetracycline media. In this technique, bacteria colonies are removed from one plate and placed in the same spatial orientation onto a new plate containing ampicillin and tetracycline (data not shown). Although there was sequence length heterogeneity, the average length of all pRAN3 substitutions, including those not selected for tetracycline, was 20 bases, close to the 19 basepairs of the synthetic DNA sequences used for mutagenesis. Therefore, greater than 90% of the 887 ampicillin resistant colonies contained promoter substitutions and about 2 of these colonies were also tetracycline resistant, suggesting that approximately 0.2% of the $10^9$ possible random sequences present in this construction may duplicate promoter recognition site activity. As expected, the absence of adenine reduced the frequency at which promoter recognition sites were selected from random sequences.

EXAMPLE 3

Correlation Between Tetracycline Resistance and Transcription of Tetracycline Resistance DNA In order to investigate the correlation of the tetracycline resistance phenotype with transcription of the tetracycline resistance gene, *E. coli* strain DH5.1 cells bearing plasmids obtained in Examples 1 and 2 and containing promoter recognition site replacements were tested for resistance to tetracycline (right-hand column of FIG. 3). The range of tetracycline resistance conferred by the plasmids selected for ampicillin resistance only (pBB3, pBB5, pBB9, pBB10, pBB13, and pBA1 through pBA10), was between 2 and 10 μg/ml. For the ampicillin/tetracycline selected plasmids (pBG8, pBT9, pBT21, and pBTR3), the range was between 30 and 60 μg/ml, while pBR322 was resistant to 40 μg/ml. Both pBT9 and pBT21 were found to be resistant to concentrations that inhibited pBR322, i.e., 50 and 60 μg/ml, respectively. Tetracycline resistance was measured using the $EOP_{50}$ method as described above in Example 1.

Figure 2:
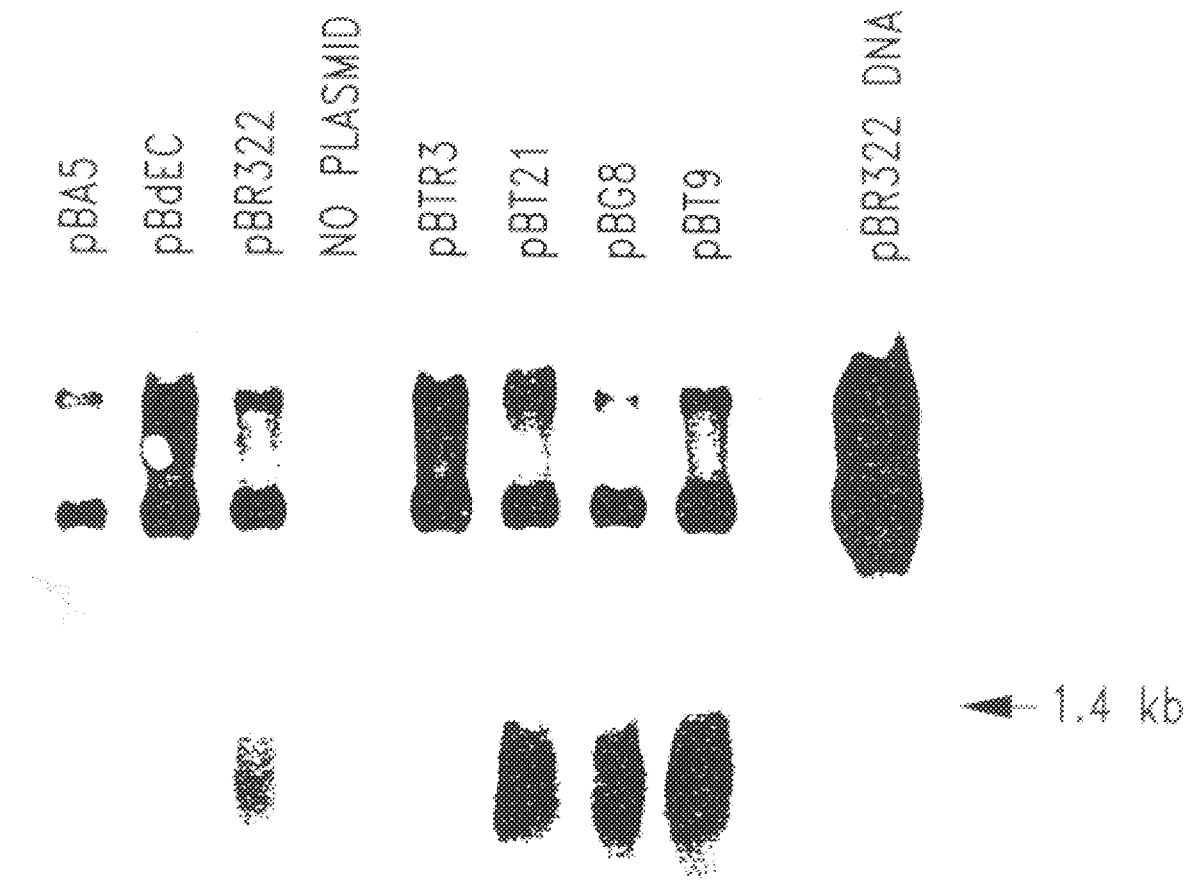
FIG. 2 is an RNA gel blot analysis quantifying tetracycline resistance gene transcription in various plasmid populations described in the Examples.

To show the direct correlation between levels of tetracycline resistance and the presence of tetracycline resistance transcript, a northern blot analysis was performed, as described above, and used to quantify transcription from the tetracycline resistance gene (FIG. 2). Cellular nucleic acids (both DNA and RNA) were probed with the 787 basepair EcoR V to Nru I restriction fragment from the protein coding region for tetracycline resistance described above in Example 1. The absence of hybridization in strain DH5.1 lacking plasmid reveals the specificity of this probe. Hybridization of nucleic acids from strain DH5.1 *E. coli* harboring pBR322 detected three bands. The two highest in molecular weight were plasmid DNA, while the third band (lowest molecular weight) contained the transcript from the tetracycline resistance gene of about 1.4 kb maximum length. DH5.1 containing either the tetracycline sensitive promoter deletion plasmid, pBdEC (Example 1), or the tetracycline sensitive promoter substitution plasmid, pBA5 (Example 2, pRAN3), revealed an absence of transcription from the tetracycline resistance gene. DH5.1 harboring the tetracycline resistance promoter substitutions, pBG8 (from pRAN4 population) and pBT9, pBT21, and pBTR3 (from pRAN3 population), exhibited a varying level of tetracycline resistance transcript. The amount of tetracycline resistance transcript for each plasmid was quantified using densitometry of the northern blot obtained. Transcript levels were normalized to plasmid DNA concentrations by taking the quotient of the values for the 1.4 kb band and the plasmid DNA bands. Table 2 shows the correlation of phenotype with transcription.

TABLE 2

| | Correlation of Phenotype and Transcription | | | | | | |
|---|---|---|---|---|---|---|---|
| Plasmid | pBT21 | pBT9 | pBG8 | pBR322 | pBTR3 | pBA5 | pBdEC |
| tetracycline resistance | 1.5 | 1.25 | 1.00 | 1 | 0.75 | 0.05 | 0.05 |
| tet$^r$ transcript | 1.27 | 1.17 | 1.01 | 1 | 0.290 | 0 | 0 |

All values are expressed relative to those obtained in pBR322. Thus, there was a direct correlation between the levels of tetracycline resistance and the tetracycline resistance transcript. Therefore, the tetracycline resistant phenotype provides a good estimate of promoter strength in these Examples.

EXAMPLE 4

Demonstration that Tetracycline Resistance is not Produced by Host Cell Mutation To verify that the promoter substitution was in fact the cause of the tetracycline resistant phenotype, and that a plasmid mutation rather than a chromosomal mutation was responsible for the phenotype, secondary transformations using plasmids purified from the primary ampicillin resistant/tetracycline resistant transformants were performed. Plasmids pBG8, pBT9, pBT21, and pBTR3 (FIG. 3) were used to transform *E. coli* strain DH5 (obtained from Bethesda Research Laboratories) using tetracycline selections with an efficiency approximately equal to that of pBR322. Therefore, tetracycline resistance was conferred by mutation of the promoter region on the plasmid, and not by mutation within the host bacteria.

Discussion

The above Examples demonstrate the usefulness of the present invention for producing novel DNA sequences capable of promoter activity by biological selection of a population of synthetic DNA fragments heterogeneous in sequence. Deletion of 19 basepairs at the −35 promoter region of the tetracycline resistance gene of pBR322 abolished transcription from the tetracycline resistance gene of the plasmid. Substitution of these 19 basepairs with random DNA sequences resulted in a maximum of $4^{19}$ ($3 \times 10^{11}$) possible replacement sequences. In a population of about 1000 bacteria that were found to harbor plasmids with these random substitutions, tetracycline selection identified several functional −35 promoter sequences. These novel promoters exhibited only partial homology to the −35 promoter consensus sequence. Further, two of the sequences (plasmids pBT9 and pBT21, FIG. 3) were found to promote transcription more strongly than the native promoter. These promoter sequences differ from all previously identified promoters and promoter mutations.

In the tetracycline resistance gene of pBG8, pBT9, and pBT21, in vivo transcription initiates ten nucleotides downstream from the pBR322 initiation site, as determined from mapping the 5' end of the tetracycline resistance mRNA using primer extension as described by McKnight et al., *Cell*, 25, pp. 385–398 (1981). Briefly, an oligonucleotide primer was hybridized to a sequence within the tetracycline resistance gene. Synthesis of a complementary strand by reverse transcription produced a DNA sequence whose length is indicative of the distance between the 5' mRNA end and the location of the known primer.

While all four of the promoter recognition regions obtained in the above Examples retain homology with the consensus sequence, in three of those sequences, pBG8, pBT9, and pBT21, the consensus alignment is shifted ten nucleotides downstream (FIG. 3). In these three promoters, in vivo transcription initiation also shifts ten nucleotides downstream. The RNA polymerase therefore recognizes a new Pribnow box from within the original pBR322 sequence. A candidate Pribnow box, ten nucleotides downstream from the original Pribnow box, is T<u>GCGGTA</u>GTT <u>T</u>, wherein agreement with the consensus sequence has been underlined. Supporting evidence comes from a mutation in the lac promoter in which a base substitution at position +1 (downstream) activates a latent Pribnow box to initiate transcription at position +13. Maquat et al., *J. Mol. Biol.*, 139, pp. 551–556 (1980).

The functional tetracycline resistance promoter in pBTR3 has conserved the consensus spacing of 17 nucleotides between the position −35 and −10 promoter elements. However, the nonfunctional tetracycline resistance promoter in pBA7 retains substantial homology with the consensus sequence, but not the spacing. These promoter mutations demonstrate the significance of the spacing between the two promoter elements.

From among the more than 150 known promoters and promoter mutations (McClure, *Ann. Rev. Biochem.*, 54, pp. 171–204 (1985)), the only "up" mutation that decreases homology to the consensus sequence is found in −35 region of the arg promoter (Horwitz et al., *J. Bacteriol.*, 142, pp. 659–667 (1980)), and there are no "down" mutations that increase homology with the consensus sequence. Among the sequences described herein, pBTR3 contains decreased homology with the consensus sequence, relative to pBR322, and is a down mutation. However, pBT9 and pBT21 contain tetracycline resistance promoters with decreased consensus homology at both promoter elements, yet are both up mutations. While these results highlight the importance of the promoter consensus sequence, they also surprisingly indicate that deviations from the consensus need not necessarily decrease promoter activity.

EXAMPLE 5

Demonstration that Synthetic DNA Sequences Function Within the Plasmid to Produce Tetracycline Resistance In order to unambiguously establish that the promoter replacements are the elements of the plasmid responsible for tetracycline resistance, one of the plasmids (pBT9) was reconstructed. Oligonucleotides of known sequence were used to duplicate the promoter substitutions (FIG. 3) found in pBT9. Two oligonucleotides, each identical to one of the two DNA strands of the promoter recognition region in this plasmid were chemically synthesized.

Construction of pBT9R. A 26-bp oligomer, 5'-AATTCTTGGGCGC-GCGTCGGCTTGAT-3' (17 µg), was annealed to a 24-bp oligomer, 5'-CGATCAAGCCGACGCGCGCCCA-AG-3' (16 µg), in a 1:1 molar ratio in a reaction mixture containing 90 mM NaCl, 15 mM tris-HCl (pH 7.9), and 1 mM MgCl$_2$ to form a total volume of 200 µl. The mixture was heated at 65° C. for 5 min and then at 57° C. for 90 min, followed by immediate chilling on ice for 15 min Incubation with T4 polynucleotide kinase in the presence to ATP was used to add 5' phosphoryl termini. Maniatis et al., supra. The resulting product contained EcoRI and Cla I cohesive ends. The synthetic 26-oligomer was of the same sequence as pBT9 in the nontemplate strand extending from the EcoRI restriction site at position −47 to the Cla I restriction site at position −21. The complementary synthetic 24-oligomer had a sequence equivalent to that of the template strand of pBT9 (position −43 to position −18). The annealed synthetic oligonucleotides were then ligated into the EcoRI and Cla I-digested pBR322. The resulting construct was designated plasmid pBT9R.

*E. coli* strain DH5 was transformed using 50 ng of pBT9R DNA to produce 353 ampicillin resistant and 114 ampicillin resistant/tetracycline resistant colonies, at an efficiency of $7 \times 10^3$ colonies/µg DNA using ampicillin selection, and $2 \times 10^3$ colonies/µg using ampicillin and tetracycline selection (Table 1C). Plasmids from 4 of the ampicillin resistance/tetracycline resistance colonies were characterized, as described above, by plasmid purification and DNA sequencing. Plasmid sizes were compared using agarose gel electrophoresis, and approximately 200 basepairs centered at about position −35 were sequenced. The results are shown in FIG. 3. Plasmids from all four colonies contained insertions in the expected region. Three colonies contained a plasmid, pBT9R, identical to that of pBT9, while the other colony contained a plasmid that included the sequence present in pBT9 but with an extra insertion of three basepairs upstream. In the absence of plasmid, DH5 was found to be resistant to a tetracycline concentration of 2 µg/ml. When harboring pBT9R, the reconstruction of pBT9, DH5 was resistant to a tetracycline concentration of 50 µg/ml, the same level of resistance which the original pBT9 conferred on DH5.1. Therefore, tetracycline resistance was conferred by the promoter substitutions and not by a mutation elsewhere on the plasmid.

Discussion

The results of the above Examples are summarized in FIG. 3. The consensus promoter sequence as previously identified by Hawley and McClure, *Nucl. Acids Res.*, 11, pp. 2237–2255 (1983), is shown on the top line of FIG. 3. The bases found to be most strongly conserved in the consensus are shown in upper case. The sequence of pBR322 is depicted next, below the consensus sequence. Following pBR322 are the substitutions for the promoter sequence obtained by insertion of the synthetic DNA sequences as described in preceding Examples. Spaces have been inserted before and after the pBR322 promoter sequence and the promoter substitutions to maximize alignment with the consensus sequence and facilitate visual comparison. Portions of sequences exhibiting homology with the consensus sequence are enclosed in boxes. Dashes indicate positions in the sequence identical to that in pBR322. Bases within the dashes which match the pBR322 indicate positions within pBR322, outside of the substitution obtained using the synthetic DNA sequences, that, together with the substitution, provide homology with the promoter consensus sequence (−35). Two plasmids, pBTR3 and pBA8, possess downstream insertions, a possible artifact from plasmid construction, indicated as subscripts in the dashes (e.g., TCC in pBTR3). Three plasmids, pBA7, pBT9, and pBT21, have two sites of potential alignment with the consensus sequence; although not aligned, bases in the alternate site are underlined in the FIGURE. Tetracycline resistance was determined as described above.

EXAMPLE 6

Selection of Novel Leader Sequences

Plasmid construction. A plasmid designated pBdBLA is constructed containing DNA encoding the gene for β-lactamase, lacking the coding region for the leader sequence for this protein, and containing a restriction endonuclease recognition site at the immediate 5' terminus of the coding region, so that synthetic, random DNA sequences may be conveniently ligated in place.

The parent plasmid pBdBLA, into which the random DNA sequences will be inserted, is constructed using techniques of M13 site directed mutagenesis similar to that described by D. M. Glover, supra. The modification of the pBR322 β-lactamase gene is more easily accomplished if the gene is temporarily transferred to a bacteriophage M13 vector. The M13mp family of bacteriophage vectors facilitates site-directed mutagenesis because they can be conveniently isolated in single-stranded form. The EcoRI to Pst I restriction fragment of pBR322 is cloned into M13mp10. The 5' portion of the β-lactamase gene is contained on the EcoRI to Pst I restriction fragment of pBR322. M13mp10 is particularly useful because it contains unique EcoRI and Pst I restriction sites. Messing, J., *Methods in Enzymology*, 101, p. 20 (1983).

Restriction endonucleases and enzymes of nucleic acid metabolism are purchased from commercial sources and used according to the manufacturers' instructions. In addition to the well-known protocols for M13 site-directed mutagenesis, standard techniques of molecular cloning are used. The plasmid pBR322 is digested with EcoRI and Pst I, and this restriction fragment is purified by electrophoresis in low melting temperature agarose. The restriction fragment is ligated into similarly digested M13mp10 vector.

Two mutagenic steps are required. The first produces a deletion of the existing leader sequence. The second produces an insertion of a unique restriction site so that the random DNA sequences may be ligated in place.

In the first step, the distal 66 bases of the 69 base DNA sequence coding for the leader polypeptide are deleted. The first three bases, functioning as an ATG initiation codon, are preserved. The mutagenic 20-mer oligonucleotide, 5'-TTTCTGGGTGCATACTCTTC-3', is hybridized to the β-lactamase gene in the single-stranded M13mp10 recombinant plasmid, so as to abridge (i.e., remove or "loop-out") the leader sequence. The mutagenic 10-mer primer consists of two 10-base-long "arms" which flank either side of the leader sequence. In vitro copying using the large (Klenow) fragment of DNA polymerase I produces a partially duplex plasmid in which one strand contains a leader sequence deletion. Complete duplication of the mutant DNA strand is accomplished in vivo. The resulting deletion is verified using standard DNA sequence analysis, as described above in Example 1.

In the second step, a mutagenic primer that is a derivative of the first primer is used to insert a unique Bgl II restriction site at the 5' terminus of the leaderless, β-lactamase gene. pBR322 lacks a Bgl II site. The mutagenic 26-mer, 5'TTTCTGGGTGAGACCTCATACTCTTC-3', is hybridized to the leaderless β-lactamase gene in the single-stranded M13mp10 recombinant plasmid, so as to insert a six-base Bgl II restriction site (5'-AGATCT-3') immediately 3' to the remaining ATG initiation codon. As above, both in vitro and then in vivo polymerization are used to complete the synthesis of the mutant DNA strand. The resulting insertion is verified by DNA sequence analysis, as above.

Finally, the mutagenized β-lactamase gene fragment is recovered from M13mp10 and reinserted into pBR322 to complete the construction of pBdBLA. The ml3mp10 recombinant plasmid is digested with EcoRI and Pst 1, and the restriction fragment is purified by agarose gel electrophoresis. The restriction fragment is then ligated into similarly digested pBR322. The resulting product, containing a leaderless β-lactamase gene (with a unique restriction enzyme adjacent to the ATG initiation codon), is verified using DNA sequence analysis.

Production of random DNA sequences. Random DNA fragments containing Bgl II compatible ends may be ligated into pBdBLA to select for leader function. To produce these random DNA fragments a 74-mer oligonucleotide, 5-GGGGAGATCT(A,C,G,T)$_{54}$AGA-TCTGGGG-3', is hybridized to a complementary 10-mer oligonucleotide, 5'-CC-CCAGATCT-3'. In a manner equivalent to that set forth above, in Examples 1 and 2, the partial duplex is copied with the large Klenow fragment of DNA polymerase I and digested using Bgl II. The restriction fragments are ligated into pBdBLA that has been cleaved with Bgl II and treated with bacterial alkaline phosphatase to produce a population of plasmids containing heterogeneous random DNA sequences inserted in place of the deleted native leader sequence.

The random stretch of 54 bases, coding for 18 amino acid residues, any of which may be one of the 20 amino acids used in protein synthesis, will allow for a maximum of $20^{18}$ (about $3 \times 10^{23}$) different possible sequences. (Four more amino acid residues, an argenine and a serine residue at both sides of these 18 residues, will be coded for by the Bgl II recognition site). Out of every 64 codons, 61/64 will not be termination codons; thus, there will be a total of $(61/64)^{18} \times 20^{18}$ (approximately $10^{23}$) random sequences that will not contain termination codons and will allow for an open reading frame. The fraction of random sequences containing open reading frames, and the residue composition (i.e., relative hydrophobicity or hydrophilicity) may be altered by biasing the DNA base composition in the random sequence. For example, because all termination codons contain adenine, a deficiency of adenine in the random stretch will greatly reduce the frequency of termination codons. Because the random insertions are of length equal to the native sequence, frameshifts are not expected.

To select those DNA sequences with secretory activity, the random plasmid population is used to transform *E. coli* using selection with ampicillin and tetracycline as described above in Example 1. Tetracycline will select for bacteria containing plasmids bearing inserts (as the pBR322 tetracycline resistance gene is left intact in pBdBLA), and ampicillin will select for functional leader sequences. The random plasmid population transforms *E. coli* strain DH5 at high efficiency (Hanahan, supra.). The tetracycline concentration in the media is 12.5 µg/ml, and ampicillin concentration is 50 µg/ml. Transformants are amplified by growth in LB at 37° C. for 1 hour (approximately two generations) prior to antibiotic selection on LB agar. Because pBdBLA contains a deletion of the leader sequence, pBdBLA will be ampicillin sensitive. Therefore, ampicillin resistant transformants will contain functional leader sequences. These novel, functional leader sequences may be further characterized by DNA sequence analysis. All resulting sequences will be flanked by Bgl II restriction sites, facilitating their transfer to other genes and/or plasmids, for further analysis or subsequent use.

The above procedure allows for the direct selection, rather than the tedious screening, of functional leader sequences. Leader sequences are thus selected from a population of synthetic random DNA, rather than from organismal DNA of known or putative secretory activity. Because novel leader sequences may be identified, useful and unique properties may be selected. For example, this technique may be used to create leader sequences capable of functioning in a wide variety of different organisms, or leader sequences that retain activity in inhospitable physical environments.

EXAMPLE 7

Selection of Novel Proteins

Plasmid Vector. The plasmid ptac-85 has been engineered for the expression of gene fragments lacking a promoter, a ribosome-binding site, and an initiation codon. Marsh, P., *Nucleic Acids Research*, 14, p. 3603 (1986), incorporated by reference herein. Another useful plasmid is pKK 233-2, available from Pharmacia Fine Chemicals (Piscataway, N.J.). Insertion of DNA at the BamH I site of this plasmid will produce an open reading frame, from which the random DNA fragments may be translated into random proteins. Recombinant ptac-85, containing inserted random DNA produced as described below, is used to transform *E. coli* strain DH5 at high efficiency. Hanahan, supra. Because ptac-85 contains an ampicillin resistance gene, growth in ampicillin will select for transformants.

Production of random DNA sequences. Long, random DNA sequences are produced using the enzyme terminal deoxynucleotidyl transferase (hereafter "TdT") or by chemical synthesis. In either case, standard techniques of molecular cloning are employed throughout. Maniatis et al., supra. All reagents and enzymes, including TdT, are available from Pharmacia, as well as from other suppliers.

TdT will catalyze the random addition of deoxynucleotide triphosphates to the 3' termini of DNA, and has previously been used to produce random protein coding DNA sequences of 400 nucleotides in length. Damiani, G., et al., *Nucleic Acids Research*, 10, pp. 6401–6410 (1982), incorporated by reference herein. Briefly, this protocol consists of the following: (i) randomly tailing with TdT a short, single-stranded random oligomer to produce a single-stranded DNA of about 900 nucleotides in length; (ii) making this single-stranded DNA double stranded by hybridizing it to the same short, single-stranded random oligomer and copying it with the large fragment of DNA polymerase I; (iii) blunt-end digesting the resulting double-stranded DNA using the single-strand-specific enzyme S1 nuclease; and (iv) ligating BamH I linkers onto the final, random, double-stranded DNA in preparation for cloning into the parent vector. Single-stranded DNA of 5 nucleotides in length ($p(dN)_6$), from a limit digest of calf-thymus DNA (Pharmacia, Piscataway, N.J.), is randomly tailed by TdT. A typical 100 µl reaction containing 50 ng $p(dN)_6$, 10 units TdT, 100 mM potassium cacodylate (pH 7.0), 1 mM $CoCl_2$, 0.2 mM dithiothreitol, and 0.25 mM of each of the deoxynucleotide triphosphates (dNTPs) is incubated for 1 hour at 37° C. This reaction produces approximately 9 µg of random DNA sequences of a mean length of approximately 900 nucleotides. The resulting product is purified by phenol/chloroform extraction and ethanol precipitation. The length of the resulting product may be verified using electrophoresis on a 1.5% agarose gel, or, if a label such as $\alpha$-$^{32}$ phosphorus is incorporated into the dNTPs, both the length and base composition of the resulting product may be determined by precipitation in 10% trichloroacetic acid. Maniatis et al., supra.

The base composition of the final product may be biased by altering the dNTP concentrations in the initial reaction. For example, to reduce the frequency of termination codons appearing in the random DNA sequences, the concentration of dATP may be reduced, because all three of the termination codons contain adenine. To make the DNA from the above reaction double-stranded, it is hybridized with a five-fold molar excess of $p(dN)_6$ in 90 mM NaCl, 15 mM tris-HCl (pH 7.9), and 1 mM $MgCl_2$ in a total volume of 120 µl by heating at 65° C. for 5 min and then 57° C. for 90 min, followed by immediate chilling on ice for 15 min The concentration of this mixture is then adjusted to 2 mM $MgCl_2$, 1 mM dithiothreitol, 100 µM of each of the dNTPs, and 25 units of the large (Klenow) fragment of DNA polymerase I in a final volume of 240 µl and incubated at 37° C. for 60 min The approximately 18 µg of double-stranded DNA produced from the above reaction is purified by phenol/chloroform extraction and ethanol precipitation. Next, the DNA is digested with the single-strand-specific S1 nuclease to ensure that it is blunt ended. The above DNA is reacted with 100 units of S1 nuclease in 200 µl containing 30 mM sodium acetate (pH 4.6), 50 mM NaCl, 1 mM $ZnCl_2$, and 5% glycerol and incubated at 37° C. for 30 min. The resulting blunt-ended, double-stranded DNA (approximately 15 µg) is purified by phenol/chloroform extraction and ethanol precipitation. To prepare the blunt-ended, double-stranded random DNA for insertion into the cloning vector, this purified DNA is ligated to BamH I linkers (Pharmacia, Piscataway, N.J.) and digested with BamH I, both done using standard techniques. Maniatis et al., supra The random DNA is next ligated into the parent vector, using standard techniques.

Growth Selection. The novel catalytic activity is identified from the above transformants by growth in a selective medium. To isolate DNA sequences encoding a novel protein capable-of conferring tetracycline resistance, the above transformants are grown on LB agar containing 12.5 µg/ml tetracycline.

One construction of a random plasmid population may suffice to select for a plurality of novel protein activities. For example, to create each new catalytic activity, only the final selection phase need be altered. Additionally, since each construction of a random plasmid population will contain a small subset of all possible protein sequences, for any given catalytic activity, each random plasmid population will yield a different protein sequence.

An alternative application of the above procedure is its use to modify only the active site of a known protein. In an entire protein DNA sequence, only a few amino acid residues (i.e., those encoding the "active site") are actually involved in enzymatic catalysis. By mutagenizing DNA encoding a gene so as to create a heterogeneous population of modified genes, each different and random in sequence at the active site, DNA sequences encoding new or modified catalytic activities may be selected.

Although targeted mutagenesis has been used by others to define the location of functional sequences within prokaryotic and eukaryotic DNA, the base changes from the wild-type sequence were limited in number, presumably because of the premise that most functional sequences resemble those already known. In these methods, new, functional DNA sequences were not produced. In contrast, the method of the present invention applies biological selection to an exceptionally large and diverse population of random DNA sequences, and enables rapid screening of large amounts of synthetic DNA to identify novel functional DNA sequences. The present method may be used to select novel sequences from large populations of possible DNA sequences, rapidly and with relatively little effort, since transformation and selection may be accomplished without requiring prior characterization of the synthetic DNA sequences inserted. Because this process allows for direct selection from large, random populations of DNA sequences, prior knowledge of structure-function relationships with respect to specific regions of DNA is not required to generate novel, functional sequences. However, the process of this invention may be used to provide information as to structure and function relationships of specific regions of DNA encoding biological activity. This invention may be used for the selection of DNA sequences encoding peptide hormones, and related effector molecules such as growth factors, leader sequences for secreted peptides, catalytic domains, genetic markers, and even entire enzymes and other proteins in prokaryotes or eukaryotes. Genetic regulatory elements, including promoters, enhancers, origins of replication, transcription terminators, centromeres, and telomeres may also be produced or evaluated by the method of this invention.

EXAMPLE 8

Mutants Generated by the Insertion of Random Oligonucleotides into the Active Site of the β-lactamase Gene We have remodeled the gene coding for β-lactamase by replacing DNA at the active site with random nucleotide sequences. The oligonucleotide replacement ($Phe^{66}XXXSer^{70}XXLys^{73}$) preserves the codon for the active serine-70 but also contains 15 base pairs of chemically synthesized random sequences that code for $2.5 \times 10^6$ amino acid substitutions (x). From a population of E. coli infected with plasmids containing these random inserts, we have selected seven new active site mutants that render E. coli resistant to carbenicillin and a series of related analogs. Each of the new mutants contains multiple nucleotide substitutions that code for different amino acids surrounding serine-70. Each of the mutants exhibits a temperature sensitive β-lactamase activity. This technique thus permits the construction of alternative active sites in enzymes based on biological selection for functional variants.

For studies on the active sites of enzymes we chose to insert random nucleotide sequences into the gene for RTEM-1 β-lactamase (EC 3.5.2.6) that is present in the plasmid pBR322 (Mathew & Hedges, 1976; see the citations listed below). Bacterial β-lactamases hydrolyze the β-lactam ring of penicillin or cephalosporin transforming them into reactive metabolites. The mechanism of catalysis by the class A enzymes involve a transient acylation of the serine residue at position 70 (Ambler, 1980). The nucleotide sequence and three dimensional structure of several class A β-lactamases have been determined (Herzberg & Moult, 1987) and indicate a high level of conservation of amino acids surrounding the active Ser-70. Schultz and Richards (1986) used site saturation mutagenesis to show that even though Thr-71 is conserved, it can be replaced by 14 of the 20 amino acids substituted. Thus, despite the evolutionary conservation of one amino acid within the active site there could be a high degree of tolerance for substitutions. β-lactams and cephalosporins are among the most frequently prescribed class of pharmaceuticals worldwide, and the rapid evolution of β-lactamases in pathogenic bacteria continues to defeat the best efforts of chemists to create new resistant analogs (Bush, 1988).

We have replaced a portion of the active site of β-lactamase in the plasmid pBR322 with an oligonucleotide that retains the codon for the active Ser-70 but also contains two flanking sequences of six and nine random nucleotides. In these experiments we have screened $2 \times 10^5$ tetracycline-resistant ($tet^r$) colonies of E. coli infected with plasmids containing random inserts and obtained seven new carbenicillin resistant mutants. DNA sequence analyses of the mutants indicate that multiple amino acid substitutions within the active site can be tolerated and are compatible with enzymatic activity. Furthermore, nucleotide substitutions involving evolutionarily conserved amino acids alter substrate specificity and temperature stability.

Experimental Procedures

Materials. Oligonucleotides were synthesized using phosphoramidite chemistry by Operon Technologies (San Pablo, California). The following two oligonucleotides, each 47 nucleotides in length, were used as templates for the construction of the random inserts:

i) 5'-CGCCCCGAGGAACGT-NNNNNNNNNNNNNNNNNNNNNAGTACTGCT-3';

ii) 5'-CGCCCCGAGGAACGTTTT-NNNNNNNNAGCNNNNNNAAAGTACTGCT-3.

The stretches of random nucleotides (designated by the Ns) within these inserts were synthesized using equimolar mixtures of nucleoside phosphoramidite derivatives. Restriction endonucleases were obtained commercially and were used according to the suppliers' instructions. Standard molecular cloning methods were employed (Maniatis, et al., 1982).

Figure 4:
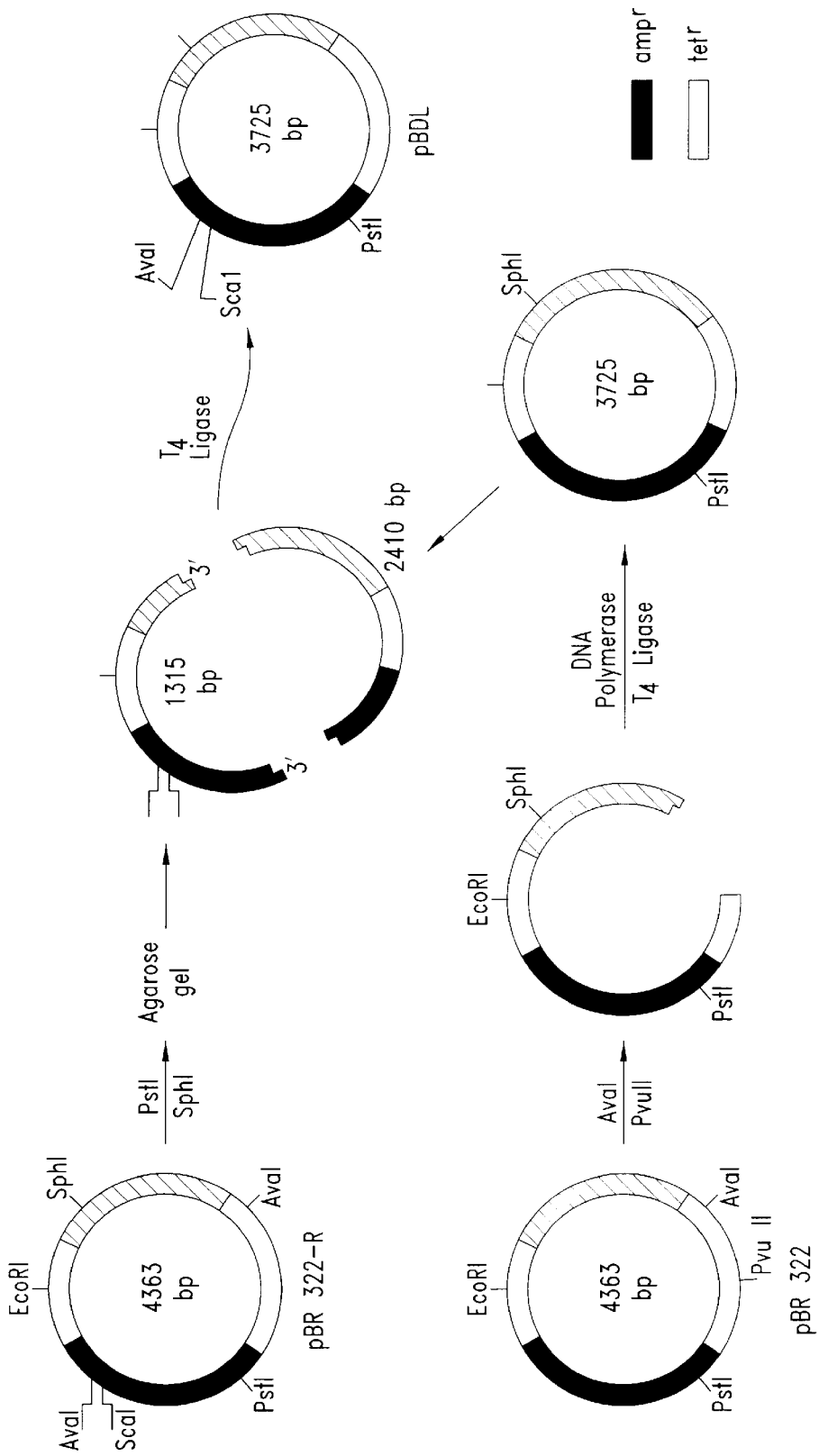
FIG. 4 shows the construction of plasmid pBDL, as described in Example 8.

Plasmid construction. The vector for the insertion of random sequences, pBDL, is a modification of pBR322 containing within the ampicillin gene two unique restriction sites located on either side of the nucleotides coding for Ser-70. pBDL was assembled by ligating together two modified segments of pBR322 (FIG. 4). The first segment was obtained from the plasmid pBR322-R, a generous gift of Dr. J. H. Richards (California Institute of Technology, Pasadena, Calif.). It is a modification of pBR322 that contains an Ava I and a Sca I site centered at positions 3972 and 3937, respectively, as well as an additional AvaI site at 1425 (Schultz & Richards, 1986). Digestion with Pst I and Sph I yielded a fragment of 1315 bp that contained a portion of the ampicillin gene and lacked the second AvaI site.

The second segment was obtained by the following steps: digestion of wild-type pBR322 with Ava I and Pvu II, purification of the large fragment by electrophoresis and electroelution, filling in the Ava I termini with *E. coli* Pol I, and blunt end ligation with T4 DNA ligase. The resultant 3725 bp plasmid was also digested with Sph I and Pst I, and the 2410 bp fragment was purified by electrophoresis and ligated onto the first segment.

Synthesis of Random Oligonucleotides. The double-stranded oligonucleotide used in the construction of the nonproducer strain, pBNP, was synthesized by hybridizing 200 ng of 9-mer primer, 5'-AGCAGTACT-3', to 1 μg of the single-stranded oligonucleotide template, 5'-CGCCCCGAGGAACGT (N)23 AGTACTGCT-3', in 20 mM Tris-HCl (pH 7.5), 10 mM MgCl$_2$, 50 mM NaCl, and 1 mM dithiothreitol at 65° C. for 10 min This template-primer was extended with the large fragment of *E. coli* Pol I, digested with Ava I and Sca I and purified by polyacylamide gel electrophoresis. The double-stranded oligonucleotide for the construction of the plasmid used in selecting new mutants was synthesized by a similar protocol: 200 ng of 9-mer primer 5'-AGCAGTACT-3' was hybridized to 1 μg of the template oligonucleotide:

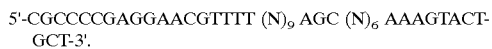
5'-CGCCCCGAGGAACGTTTT (N)$_9$ AGC (N)$_6$ AAAGTACT-GCT-3'.

The template-primer was extended with *E. coli* Pol I, digested with Ava I and Sca I, and used as a replacement for the insert in the nonproducer strain.

Other Methods. The preparation of competent DH5α and DH5 *E. coli* and subsequent transformation with plasmid DNA were carried out according to the protocol of Hanahan (1983). Transformants were grown in "SOC" medium for 1 hr prior to antibiotic selection. We scored for carbenicillin resistance by incubating the transfected *E. coli* in petri dishes in agar containing 12.5 μg/ml tetracycline and 50 μg/ml carbenicillin at 30° C. for 48 hrs. Plasmid DNA was purified by the alkaline lysis method (Maniatis, et al., 1982), and sequencing of both strands was carried out on double-stranded DNA purified by isopicnic density centrifugation using dideoxy chain termination (Sanger, et al., 1977). β-lactamase activity was scored using the chromogenic cephalosporin: pyridinium-2-azo-p-dimethyl aniline chromophore (PADAC) (Kobayashi, et al., 1988). An overnight culture of each test mutant was diluted 1,000-fold with the fresh broth, and a 5 μl inoculum ($10^{-4}$ CFU per spot) of each sample was applied onto agar plates containing 50 μM PADAC and 12.5 μg/ml tetracycline. After 18–20 hr incubation at 30° C. the diameter of the PADAC hydrolysis zone formed around the colony was determined. The highest antibiotic concentration permissible for growth of *E. coli* was determined using antibiotic concentration gradients generated in L-agar plates (Schultz, 1987).

Results

In order to substitute random DNA sequences for designated nucleotides at the active site of the β-lactamase gene we first constructed a derivative of plasmid pBR322 that contains two unique restriction sites flanking the targeted sequence (see Experimental Procedures). The new DNA vector contained both the tetracycline and ampicillin resistance genes. Within the ampicillin resistance gene are Ava I and Sca I sites centered at positions 3329 and 3294, respectively. Since it is likely that only a small fraction of random nucleotide sequences at the active site of β-lactamase code for viable amino acid substitutions, and since it is difficult to completely cleave restriction sites when present at the ends of double-stranded DNA (Horwitz & Loeb, 1986), we designed a two step strategy to minimize contamination with wild-type sequences. We first constructed a nonproducer plasmid, pBNP, that contains an inactive nucleotide replacement, obtained DNA from isolated clones, and then exchanged the inactive sequence with a random nucleotide sequence to be used for mutant selection.

Figure 5A:
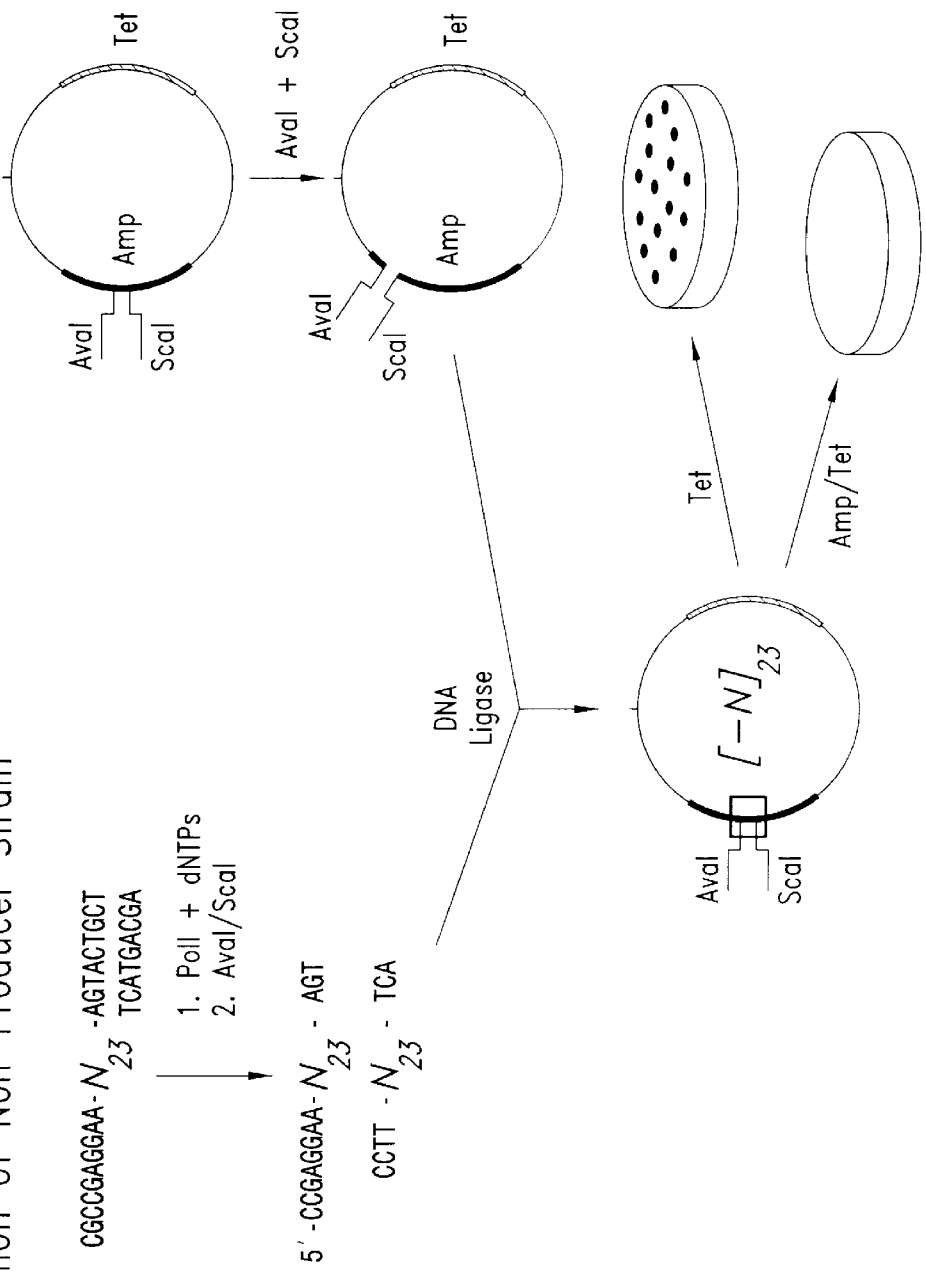
FIGS. 5A and 5B illustrates the overall scheme for the insertion of oligonucleotides containing random DNA inserts described in Example 8, with (A) Step I showing construction of the nonproducer strain pBNP, and (B) Step II showing replacement of the oligonucleotide in the nonproducer strain with random DNA sequences, wherein amp=ampicillin, tet=tetracycline, and n=unspecified bases.

The nonproducer was obtained by digesting the modified pBR322 (FIG. 4) with Ava I and Sca I and inserting a double-stranded 47 oligomer that contains a 23 base random nucleotide sequence (FIG. 5A). Plasmid infected *E. coli* were selected based on resistance to tetracycline and then screened for sensitivity to low concentrations of carbenicillin (10 μg/ml). A tet$^r$ clone was selected that was sensitive to all of the analogs tested and exhibited no detectable β-lactamase activity (FIG. 6). DNA sequence analysis demonstrated that this clone contains a 23 base pair insert between Arg-66 and Val-74 (the Ava I and Sca I sites) and codes for an amino acid sequence having no homology with the wild type sequence and also containing a single base frameshift at the carboxy terminus of the insert.

Figure 5B:
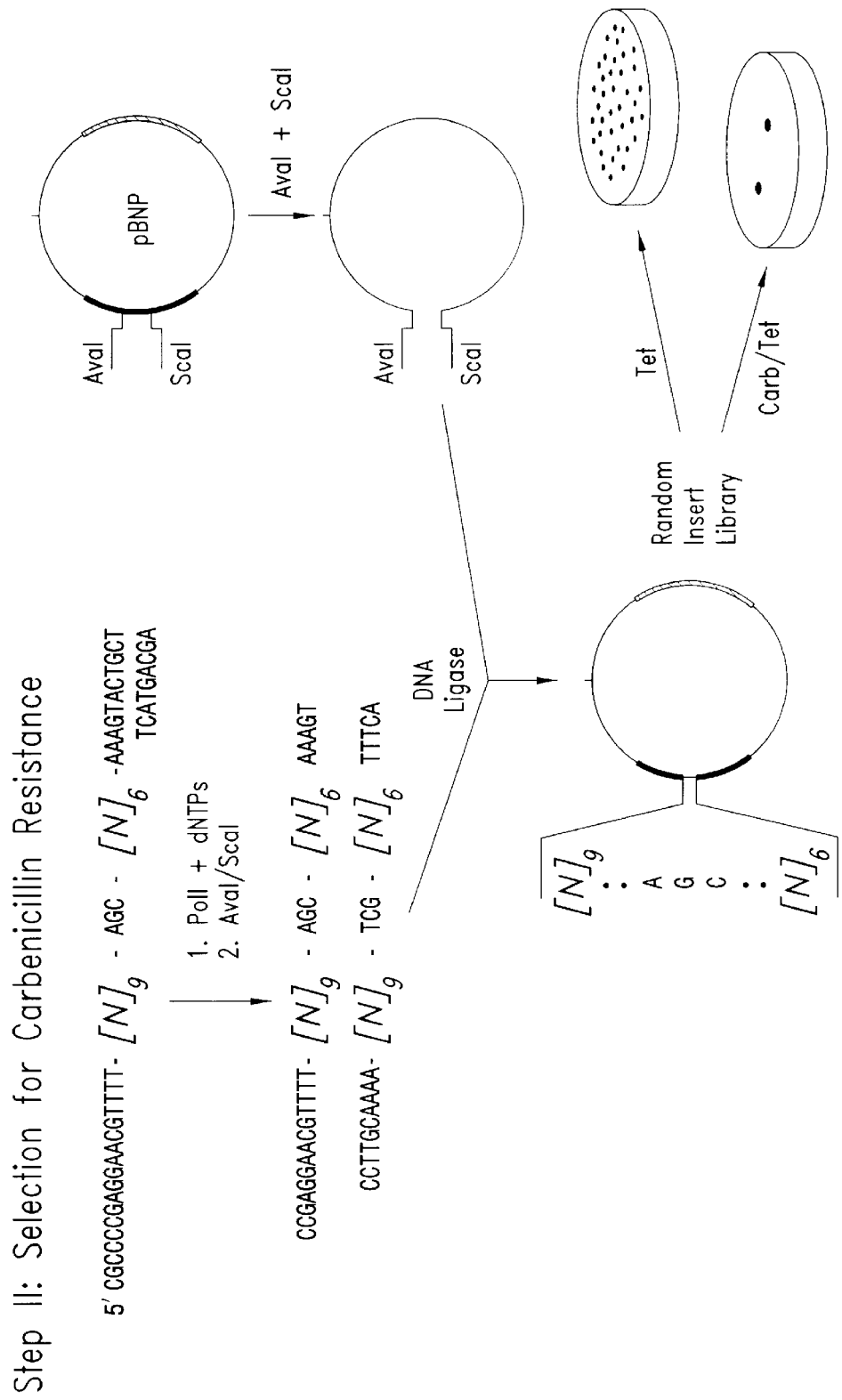

For the construction of active site mutants, DNA from the nonproducer strain was digested with the same two restriction enzymes and purified by agarose gel electrophoresis. Into this DNA was ligated an oligonucleotide containing an AGC codon for serine flanked by stretches of nine and six random nucleotides (FIG. 5B). Nonselective growth in the presence of tetracycline in four separate experiments yielded a total of approximately $2 \times 10^5$ colonies. Seven of the tetracycline resistant colonies were also resistant to carbenicillin (50 μg/ml) (FIG. 6, mutants 1–7). Each of the carbenicillin resistant clones contained the AGC codon at amino acid position 70. The distribution of nucleotides within the random positions in the mutants is: 39% C, 28% T, 23% A, and 10% G. The less than equal representation of G in the coding strand of the insert could be the result of a bias in the incorporation of nucleotides during chemical synthesis or could be indicative of the repertoire of substitutions that yield active molecules. Considering all seven mutants, 53% of the nucleotides in the random positions do not correspond to those in the parent strain. Of the 35 codons capable of being substituted, 32 contained nucleotide substitutions; 10 of these were silent, and 22 resulted in amino acid changes. Of the five substituted amino acids, the proline at position 67 is the most conserved; however, it is still lacking in one of the new sequences.

The resistance of *E. coli* infected with each of the mutant DNAs was quantified by observing the extent of bacterial growth on agar plates containing concentration gradients of carbenicillin, ampicillin or benzylpenicillin. At 30° C., the control strain, pBDL, was resistant to each of the antibiotics at >500 μg/ml, while the nonproducer strain, pBNP failed to grow at the lowest concentration in the gradient. The extent of resistance was confirmed by using agar plates containing defined concentrations of each of the antibiotics. At 30° C., mutants 2, 3, 4, and 6 rendered *E. coli* resistant to the highest concentration of antibiotic tested. However, at the elevated temperatures, all of the mutants were more sensitive to the antibiotics than was the control, pBDL. Mutant #7 was the most sensitive to each of the antibiotics. All the other mutants are more resistant towards carbenicillin than ampicillin or benzylpenicillin, particularly at higher temperatures. A chromogenic cephalosporin, PADAC, was used to measure β-lactamase activity of each of the mutant-infected *E. coli*. In general, the resistance of the mutants to carbenicillin and the other β-lactam antibiotics parallels the production by β-lactamase as measured by the hydrolysis of PADAC. However, differences in the relative resistance of the mutants to the different analogs suggest that some of the β-lactamase mutants exhibit altered substrate specificity.

To unambiguously establish that the replacement at the active site was responsible for the carbenicillin resistance in plasmid-infected *E. coli*, we reassembled one of the new mutants. We chemically synthesized a double-stranded oligonucleotide identical to the sequence of nucleotides in mutant #1 (FIG. 6). This oligonucleotide was used to replace the insert in the nonproducer strain. A comparison of the drug resistance of *E. coli* infected with mutant #1 containing the biologically selected random sequence and that bearing the chemically synthesized insert (Mutant 1R) is included in the following Table 3. The pattern of resistance is identical. Thus, antibiotic resistance is conferred by the substitution at the active site and not by some other mutation within the plasmid or within the *E. coli* chromosome.

the Ser-70 in β-lactamases evolved from an ancestral enzyme containing cysteine and, in fact, substitution of Ser-70 with cysteine yields a β-lactamase with 1–2% of the activity of the wild type parent (Sigal, et al., 1982). In six out of the seven mutants we have obtained, the most conserved amino acid is Pro-67 followed by Thr-71 (four of seven). Even though Thr-71 is conserved in Class-A β-lactamases, it has been reported that 14 out of 19 single amino acid replacements at this site yield active enzyme (Schultz & Richards, 1986). Our finding that four of the seven random mutants contain codons other than Thr confirms that threonine is not essential for catalysis.

The amino acids within the active site that determine the substrate specificity of β-lactamase are unknown. The differences in resistance to β-lactam antibiotics among the mutants we have obtained suggest that some of the mutants

TABLE 3

Maximum level of resistance and PADAC hydrolysis zone of strains with mutations at β-lactamase

| | Maximal antibiotic concentration (mg liter) permitting bacterial growth | | | | | | | | | Diameter of PADAC hydrolysis zone |
|---|---|---|---|---|---|---|---|---|---|---|
| | Carbenicillin | | | Ampicillin | | | Benz. Penicillin | | | (mm) |
| Strain/Mutant | 30° | 37° | 42° | 30° | 37° | 42° | 30° | 37° | 42° | 30° |
| WildType | >500 | >500 | >500 | >500 | >500 | >500 | >500 | >500 | >500 | 20 |
| Non Producer | NG | NG | NG | NG | NG | NG | NG | NG | NG | <4 |
| Mutant #1 | >500 | 75 | NG | >500 | 100 | NG | 250 | NG | NG | <4 |
| Mutant #1R | >500 | 75 | NG | >500 | 100 | NG | 250 | NG | NG | <4 |
| Mutant #2 | >500 | >500 | 200 | >500 | >500 | 80 | >500 | >500 | 50 | 14 |
| Mutant #3 | >500 | >500 | 70 | >500 | 160 | NG | >500 | NG | NG | 10 |
| Mutant #4 | >500 | >500 | 220 | >500 | 330 | 75 | >500 | 40 | NG | 6 |
| Mutant #5 | 320 | 83 | NG | 400 | 55 | NG | 250 | NG | NG | <4 |
| Mutant #6 | >500 | >500 | 75 | >500 | 420 | NG | >500 | 170 | NG | 6 |
| Mutant #7 | 110 | NG | NG | 310 | 100 | NG | 190 | NG | NG | <4 |

Antibiotic resistance was determined by concentration gradients, as described in Experimental Procedures. In Table 3, NG=no growth observed. PADAC hydrolysis of less than 4 mm in diameter could not be visualized due to growth of bacteria. One of the mutant sequences was duplicated into a second plasmid to rule out mutations outside the site of random sequence insertion. The insert of mutant #1 was reconstructed in plasmid pBNP by ligating into it a double stranded oligonucleotide: 47-mer 5'-CGCCCCGAGGAACGTTTTCCCGTCATGAGCATC-ATCAAAGTACTGCT-3', and its complement. The double stranded oligo was constructed as described in Experimental Procedures, and then digested with Ava I and Sca I before ligation.

Discussion

We have replaced nucleotide sequences within the active site of the β-lactamase gene with random chemically synthesized DNA sequences, and selected from a heterogeneous population those sequences that render *E. coli* resistant to carbenicillin. The nucleotide sequence of each of the new mutants has many differences from that of the parental plasmid and from any natural β-lactamases so far reported (Bush, 1988; Brenner, 1988; Kelly, et al., 1980; Spratt & Cromie, 1988; Nicholas & Strominger, 1988). This supports the notion that the active sites of enzymes may be more flexible than is generally recognized. As designed, each of the mutants maintained the codon for Ser-70 present within the oligonucleotide insert. Brenner (1988) hypothesized that have an altered substrate specificity (Table 3). The region extending from Ser-70 to Lys-73 may not be involved in substrate recognition; this region is conserved in natural β-lactamases that exhibit differences in substrate specificity (Dale, et al., 1985; Spratt & Cromie, 1988; Nicholas & Strominger, 1988). Alternatively, mutations within the region from Pro-66 to Ser-70 may be those responsible for alterations in substrate specificity. However, this sequence from Ser-70 to Lys-73 may be required for enzyme stability. In the studies of Schultz and Richards, most—but not all—substitutions for Thr-71 resulted in decreased activity at elevated temperatures, and evidence was presented that this resulted from increased proteolysis (Schultz & Richards, 1986). We observed a similar thermal lability of mutants selected from the active-site inserts that contained random nucleotide sequences in this region. Further studies will be required to determine which substitutions reduce the stability of the β-lactam resistant phenotype and if this thermal inactivation results from enzyme denaturation or increased susceptibility to proteolysis. Most of the mutants exhibited a greater resistance towards carbenicillin than the other analogs, particularly at 40° C. (Table 3), and this could be the result of selection by carbenicillin. Alternatively, carbenicillin could protect against thermal denaturation by preferentially binding to β-lactamases; the $K_m$ for carbenicillin, ampicillin, and benzylpenicillin have been reported to be 10, 31, and 21 μM, respectively (Labia, et al., 1979).

This use of random DNA for the generation of new mutants is based on the hypothesis that multiple amino acid substitutions can be tolerated within the active sites of enzymes, and that many of these substitutions could yield enzymes with altered or even new catalytic activities. Consider a chronology of selective prebiotic evolutionary events that might offer advantages to sequences with the best fit. Assume that an average gene was initially coded by 2000 nucleotides and thus was selected for from a reservoir of $4^{2000}$ possible permutations. Early steps in selection could involve DNA and RNA structure, replication, and transcription (Orgel, 1986; Eigen & Schuster, 1977). Selections based on protein structure and specificity of catalysis are likely to be relatively late events, and might be limited by the interdependence of metabolic pathways and by the stringencies of protein-protein interactions in multicomponent systems. A smaller number of possible permutations would be obtained if genes were assembled in units on the basis of structural domains (Schultz, et al., 1987; Savageau, 1986). In either case, as a consequence of progressive selective processes, a large number of the potential nucleotide arrangements that were eliminated early in evolution may nevertheless code for active enzymes.

The overall frequency of multiple amino acid codon substitutions in the random collection of β-lactamase mutants is much higher than that found in nature. By selecting active genes from random DNA inserts it might be possible to circumvent the sequential selective pressures that have occurred during evolution. Using a series of small random oligonucleotide inserts we should be able to identify most substitutions that yield reactive molecules and thus define the topology of the active site on enzymes. Small changes in the structural configuration at the active site may have profound influences on the rates and specificities of enzymatic reactions and/or thermo- and proteolytic stability. New active sequences selected from random DNA inserts might be able to catalyze reactions at a rate greater than that of the native enzymes or might utilize unusual substrates and thus be of practical importance.

Citations

Ambler, R. P. (1980) Philos. Trans. R. Soc. London Ser. B 289, 321–331.
Brenner, S. (1988) Nature 334, 528–530.
Bush, K. (1988) Rev. Infect. Diseases 10, 681–690.
Craik, C. S., Largeman, C., Flecher, T., Roczniak, S., Barr, P. J., Fletterick, R. & Rutter, W. J. (1985) Science 228, 291–297.
Dalbadie-McFarland, G., Neitzel, J. & Richards, J. H. (1986) Biochemistry, 25, 332–338.
Dale, J. W., Godwin, D., Mossakowska, D., Stephenson, P. & Wall, S. (1985) FEBS Lett. 191, 39–44.
Eigen, M. & Schuster, P. (1977) Naturwissenschaften, 64, 541–565.
Hanahan, D. (1983) J. Mol. Biol. 166, 557–580.
Herzberg, O. & Moult, J. (1987) Science, 236, 694–701.
Horwitz, M. S. Z. & Loeb, L. A. (1986) Proc. Natl. Acad. Sci. USA 83, 7405–7409.
Horwitz, M. S. Z. & Loeb, L. A. (1988a) J. Biol. Chem., 263, 14724–14731.
Horwitz, M. S. Z. & Loeb, L. A. (1988b) Science, 241, 703–705.
Horwitz, M. S. Z., Dube, D. K. & Loeb, L. A. (1989) Genome in press.
Kelly, J. A., Dideberg, O., Charlier, P., Wery, J. P., Libert, M., Moews, P. C., Knox, J. R., Duez, C., Fraipont, C. L., Joris, B., Dusart, J., Frere, J. M. & Ghuysen, J. M. (1980) Science, 231, 1429–1431.
Kobayashi, S., Arai, S., Hayashi, S. & Sakaguchi, T. (1988) Antimicrob. Agent & Chemo. 32, 1040–1045.
Labia, R., Barthelemy, M., Fabre, C., Guionie, M. W. & Peduzzi, J. (1979) IN: Beta-Lactamases (Eds., Hamilton-Miller, J. M. T. and Smith, J. T.), Academic Press, New York, pp. 429–442.
Maniatis, T., Firtsch, E. F. & Sambrook, J. (1982) Molecular Cloning: A Laboratory Manual (Cold Spring Harbor Laboratory, Cold Spring Harbor, N.Y.).
Mathew, M. & Hedges, R. W. (1976) J. Bacteriol. 125, 713–718.
Nicholas, R. A. & Strominger, J. L. (1988) Rev. Infect. Diseases 10, 733–745.
Oliphant, A. R. & Struhl, K. (1988) Meth. Enzymol. 155, 568–582.
Orgel, L. L. (1986) J. Theor. Biol., 123, 127–139.
Perry, L. J. & Wetzel, R. (1984) Science 226, 555–557.
Sanger, F., Nicklen, S., & Coulson, A. R. (1977) Proc. Natl. Acad. Sci. USA, 74, 5463–5467.
Savageau, M. A. (1986) Proc. Natl. Acad. Sci. USA, 83, 1198–1202.
Schneider, T. D. & Stormo, G. D. (1989) Nucleic Acids Res., 17, 659–674.
Schultz, S. C. & Richards, J. H. (1986) Proc. Natl. Acad. Sci. USA 1588–1592.
Schultz, S. C., Dalbadie-McFarland, G., Neitzel, J. J. & Richards, J. (1987) Proteins 2, 290–297.
Sigal, I. S., Harwood, B. G. & Arentzen, R. (1982) Proc. Natl. Acad. Sci., USA 79, 7156–7160.
Spratt, B. G. & Cromie, K. D. (1988) Rev. Infect. Diseases 10, 699–711.

While the present invention has been described in conjunction with the preferred embodiments, one of ordinary skill, having read the foregoing specification, will be able to effect various changes, substitutions of equivalents, and alterations to the methods set forth herein. It is therefore intended that the protection granted by Letters Patent hereon be limited only by the appended claims and equivalents thereof.

The embodiments of the invention in which an exclusive property or privilege is claimed are defined as follows:

1. A method of obtaining an oligonucleotide that confers a predetermined biological function on a cell, comprising:

(a) cloning into an expression vector a heterogeneous pool of oligonucleotides, x+y+z nucleotides in length, said oligonucleotides comprising a 5' randomized sequence x nucleotides in length, a central sequence y nucleotides in length, and a 3' randomized sequence z nucleotides in length, said heterogeneous pool having nucleic acid sequences representing a random sampling of the $4^{x+z}$ possible sequences for oligonucleotides of said length, wherein said cloned oligonucleotides are transcribed or act as a regulatory sequence:

(b) introducing a random sampling of said cloned heterogeneous pool of oligonucleotides into a population of cells that do not exhibit the predetermined biological function, (c) thereafter biologically selecting said population of cells for a subpopulation of cells exhibiting said predetermined biological function by contacting the population of cells with a selective medium in which only cells exhibiting the predetermined biological function survive, and (d) isolating from said subpopulation of cells an oligonucleotide comprising said central sequence and that confers said predetermined biological function; wherein said predetermined biological function is regulation of expression or a biological activity of a polypeptide.

2. A method of obtaining an oligonucleotide that confers a predetermined biological function on a cell, comprising:

(a) cloning into an expression vector a heterogeneous pool of oligonucleotides, n nucleotides in length wherein n is 54 or fewer nucleotides, from a mixture of nucleotides consisting essentially of a% adenine, t% thymidine, c% cytosine, and g% guanine, wherein a+t+c+g=100%, said heterogeneous pool having nucleic acid sequences representing a random sampling of the $4^n$ possible sequences for oligonucleotides of said length generated from nucleotides of said relative percent concentrations, wherein said cloned oligonucleotides are transcribed or act as a regulatory sequence;

(b) introducing a random sampling of said cloned heterogeneous pool of oligonucleotides into a population of cells that do not exhibit the predetermined biological function;

(c) thereafter biologically selecting said population of cells for a subpopulation of cells exhibiting said predetermined biological function, by contacting the population of cells with a selective medium in which only cells exhibiting the predetermined biological function survive; and (d) isolating from said subpopulation of cells an oligonucleotide that confers said predetermined biological function; wherein said predetermined biological function is regulation of expression or a biological activity of a polypeptide.

3. A method of obtaining an oligonucleotide that confers a predetermined biological function on a cell, comprising:

(a) cloning into an expression vector a heterogeneous pool of oligonucleotides, n nucleotides in length wherein n is 54 or fewer nucleotides, having nucleic acid sequences representing a random sampling of the $4^n$ possible sequences for oligonucleotides of said length, wherein said cloned oligonucleotides are transcribed or act as a regulatory sequence;

(b) introducing a random sampling of said cloned heterogeneous pool of oligonucleotides into a population of cells that do not exhibit the predetermined biological function;

(c) thereafter biologically selecting from the population of cells a subpopulation of cells exhibiting the predetermined biological function, by contacting the population of cells with a selective medium in which only cells exhibiting the predetermined biological function survive; and (d) isolating from the selected subpopulation of cells an oligonucleotide that confers the predetermined biological function; wherein said predetermined biological function is regulation of expression or a biological activity of a polypeptide.

* * * * *